US012560607B2

(12) United States Patent
Chao et al.

(10) Patent No.: US 12,560,607 B2
(45) Date of Patent: Feb. 24, 2026

(54) RECOMBINANT VIRUSES, INSECT CELLS AND THEIR USES IN VIRAL DETECTION AND VACCINATION

(71) Applicant: Academia Sinica, Taipei (TW)

(72) Inventors: Yu-Chan Chao, Taipei (TW);
Sung-Chan Wei, New Taipei (TW);
Huei-Ru Lo, New Taipei (TW);
Chih-Hsuan Tsai, Pingtung County
(TW); Yu-Wen Lo, Taoyuan (TW);
Wei-Ting Hsu, Miaoli County (TW);
Chuan-Yu Liao, Taipei (TW)

(73) Assignee: Academia Sinica, Taipei (TW)

( * ) Notice: Subject to any disclaimer, the term of this patent is extended or adjusted under 35 U.S.C. 154(b) by 747 days.

(21) Appl. No.: 17/913,986

(22) PCT Filed: Mar. 22, 2021

(86) PCT No.: PCT/US2021/023527
§ 371 (c)(1),
(2) Date: Sep. 23, 2022

(87) PCT Pub. No.: WO2021/194992
PCT Pub. Date: Sep. 30, 2021

(65) Prior Publication Data
US 2023/0160892 A1      May 25, 2023

Related U.S. Application Data

(60) Provisional application No. 62/993,983, filed on Mar. 24, 2020.

(51) Int. Cl.
| | |
|---|---|
| *G01N 33/569* | (2006.01) |
| *A61K 39/00* | (2006.01) |
| *C07K 14/005* | (2006.01) |
| *C07K 14/435* | (2006.01) |
| *C12N 15/86* | (2006.01) |

(52) U.S. Cl.
CPC ..... *G01N 33/56983* (2013.01); *C07K 14/005* (2013.01); *C07K 14/43572* (2013.01); *C12N 15/86* (2013.01); *A61K 39/00* (2013.01); *C12N*

*2710/14022* (2013.01); *C12N 2710/14042* (2013.01); *C12N 2710/14052* (2013.01); *C12N 2770/20034* (2013.01); *G01N 2469/20* (2013.01)

(58) Field of Classification Search
CPC ......... G01N 33/56983; G01N 2469/20; C07K 14/005; C07K 14/43572; C12N 15/86; C12N 2710/14022; C12N 2710/14042; C12N 2710/14052; C12N 2770/20034; A61K 39/00
See application file for complete search history.

(56) References Cited

U.S. PATENT DOCUMENTS

| | | | | |
|---|---|---|---|---|
| 5,888,513 A * | 3/1999 | Plana Duran | ........ | C07K 14/005 |
| | | | | 435/235.1 |
| 6,245,528 B1 * | 6/2001 | Chao | ...................... | C12N 15/86 |
| | | | | 435/235.1 |
| 6,368,825 B1 * | 4/2002 | Chao | ...................... | C12N 15/86 |
| | | | | 435/235.1 |
| 7,223,560 B2 * | 5/2007 | Chao | ................... | G01N 33/5008 |
| | | | | 435/235.1 |
| 11,123,424 B2 * | 9/2021 | Chao | ...................... | C12N 15/86 |
| 2003/0082144 A1 * | 5/2003 | Chao | ...................... | C12N 15/86 |
| | | | | 435/320.1 |
| 2003/0232035 A1 * | 12/2003 | Dubensky, Jr. | ........ | C07K 14/47 |
| | | | | 435/456 |
| 2005/0208066 A1 * | 9/2005 | Chao | ................... | C07K 14/005 |
| | | | | 435/235.1 |
| 2007/0202099 A1 * | 8/2007 | Inooka | ................... | A61P 19/00 |
| | | | | 514/12.4 |
| 2022/0249648 A1 * | 8/2022 | Chao | ................... | C07K 14/005 |

* cited by examiner

*Primary Examiner* — Janet L Andres
*Assistant Examiner* — Carey Alexander Stuart
(74) *Attorney, Agent, or Firm* — NZ Carr Law Office

(57) ABSTRACT

Provided herein are recombinant viruses and/or insect cells suitable for detecting the infection of a pathogen in a biological sample of a test subject. The information derived from the detection may also be used to render a diagnosis on whether the test subject is infected with the pathogen or not, so that proper course of treatment may be assigned to the subject. Also provided herein is a vaccine for the prophylaxis and/or treatment of infection caused by the pathogen.

10 Claims, 15 Drawing Sheets

(A) Construct 1: 6xHis at C-terminus, viral TM at N-terminus

(B) Construct 2: 6xHis at N-terminus, Viral TM at C-terminus

(C) Construct 3: 6xHis at N-terminus, GP64 TM at C-terminus

(A)

(B)

(A)

(B)

(A)

(B)

(A)

(B)

(A)

(B)

(A)

(B)

(A)

(B)

(A)

(B)

(A)

(B)

(A)

(B)

RECOMBINANT VIRUSES, INSECT CELLS AND THEIR USES IN VIRAL DETECTION AND VACCINATION

CROSS-REFERENCE TO RELATED APPLICATIONS

This application is a U.S. National Stage Filing under 35 U.S.C. 371 from International Patent Application Serial No. PCT/US21/23527, filed Mar. 22, 2021, and published on Sep. 30, 2021, which claims the priority of U.S. Ser. No. 62/993,983, filed Mar. 24, 2020, the disclosure of which are incorporated by reference herein in their entireties.

BACKGROUND OF THE INVENTION

1. Field of the Invention

The present disclosure relates to recombinant viruses. More particularly, the disclosure relates to a recombinant virus and/or an insect cell independently having at least one viral protein of a virus of interest expressed thereon, and its uses in detecting the antibodies elicited by said virus in biological samples and preventing a subject from infection caused by said virus.

2. Description of Related Art

Viruses are devastating human and animal pathogens, such as influenza viruses, EBOLA viruses, dengue and Zika viruses, coronaviruses are all dangerous viruses. Presently, most methods of detecting these viruses involve cultivating and isolating the pathogens from their hosts and sequencing the viruses' DNA to confirm their identities. Since many of these viruses are highly contagious and lethal, to protect the first-line operator, the isolation and identification must be performed in facilities that comply with at least level 2 biocontainment precautions (e.g., biosafety level 3 (BL3) laboratory). Furthermore, cultivating and isolating these viruses is time-consuming, and DNA sequencing requires well-trained technician and sophisticated equipment, rendering the present available detecting methods unsuitable for use in the clinical facility or in the field.

In some cases, purified viral proteins are used as antigens for detecting the antibody induced by the deadly viruses. However, producing purified viral proteins is also time-consuming and labor-intensive, thus is not an economically efficient way for use in the field.

In view of the above, there exist in this art a need of safe and easy-to-use agents and/or methods for detecting viruses, particularly the dangerous and lethal viruses, such agents and/or methods do not require BL3 level facility, nor the expensive and fragile DNA sequencing equipment, while at the same time may provide a result in a much shorter time frame, so that treatments and/or quarantine may be deployed in a timely manner to treat the infected subject and prevent the diseases and/or pathogens from spreading.

SUMMARY

The following presents a simplified summary of the disclosure in order to provide a basic understanding to the reader. This summary is not an extensive overview of the disclosure and it does not identify key/critical elements of the present invention or delineate the scope of the present invention. Its sole purpose is to present some concepts disclosed herein in a simplified form as a prelude to the more detailed description that is presented later.

The present disclosure relates in general to the preparation of recombinant viruses and/or cells independently having at least one exogenous pathogenic viral protein expressed thereon, as well as uses of such recombinant viruses and/or cells for the diagnosis of pathogenic infection, or for the prophylaxis or treatment of a subject suffering from said pathogenic infection.

The present disclosure is based on the discovery that a recombinant virus and/or cells independently bearing at least one viral protein of a pathogen, particularly the pathogen that requires at least level 2 biocontainment precautions, on its surface, may serve as antigens for the detection of infection from such highly lethal pathogens. Accordingly, the recombinant virus and/or cells of the present disclosure provide a fast, safe, easy-to-use, and economically efficient tool for detecting such infections without putting the first-line operators at risk of being exposed to highly dangerous pathogens. The detection also serves the purpose of rendering early diagnosis on whether a test subject is infected with such pathogen, so that necessary measures (e.g., medicaments, quarantine and etc) may be timely deployed to treat the subject and to contain the disease or pathogen from spreading. Further, the recombinant virus and/or cells of the present disclosure may also be used to identify a candidate drug suitable for the development of a medicament for treating infection caused by such pathogen.

Accordingly, the first aspect of the present disclosure is directed to a recombinant virus, which is characterized in having at least one exogenous viral protein of a pathogen expressed on its surface. The recombinant virus comprises a first promotor, and a first nucleic acid encoding the exogenous viral protein operably linked to the promoter, wherein the promoter comprises at least one promoter of a gene selected from the group consisting of hr1-hsp70, hsp70, p10, polyhedrin (p-polh), CMV, SV40, RSV, pTriEx, AcMNPV-ie1, WSSV-ie1, gp64, and pag.

According to preferred embodiments of the present disclosure, the first promoter comprises the promotor of p10 gene, and the promoter of hr1-hsp70 gene. In other embodiments, the first promoter comprises the promotor of pTriEx gene. In further embodiments, the first promoter comprises the promotor of polyhedrin gene.

Alternatively or optionally, the recombinant virus may further comprise a second nucleic acid disposed upstream to the first nucleic acid, in which the second nucleic acid encodes a signal peptide selected from the group consisting of a honeybee melittin signal peptide (HM/HBM), a GP64 signal peptide, a cecropin B signal peptide, and a GRP78/BiP signal peptide. In some embodiments, the signal peptide is HM/HBM. In other embodiments, the signal peptide is GP64 signal peptide.

Alternatively or optionally, the recombinant virus may further comprise a third nucleic acid encoding a cytoplasmic tail domain (CTD) of a baculovirus glycoprotein GP64 operably linked to the promotor.

According to embodiments of the present disclosure, the virus may be a baculovirus, a lentivirus, an adenovirus, an adeno-associated virus, a herpes virus, or a vaccinia virus. Preferably, the recombinant virus of the present disclosure is a recombinant baculovirus having at least one exogenous viral protein of a pathogen expressed on its surface.

Examples of the exogenous viral protein that may be expressed on the surface of the present recombinant virus include, but are not limited to, VP1 from adenovirus 14; capsid L1 from human papillomaviruses 16; VP1 from Simian vacuolating virus 40 (SV40); envelope protein from Epstein-Barr virus (EBV) or human monkeypox virus; VP1 or VP2 from parvovirus B19; ORF2 from Torque teno virus (TT); Cap from porcine circovirus type 2 (PCV2); Capsid from Gemycircularvirus SL1; ORF1 coat protein from human picobirnavirus; VP1 from enterovirus 71 (EV71), poliovirus, or Norwalk virus; envelope protein E1 from chikungunya virus or Rubella virus; S or N protein from coronavirus; Capsid protein VP34 from Astrovirus; ORF2 from Hepatitis E virus; E or NS1 proteins from flaviviruses; G protein from Lassa virus; HA or NA from Influenza virus A or Influenza virus B; H protein from Measles virus; G protein from Nipah virus, HN from Human parainfluenza virus 3 or Mumps virus; nucleoprotein (NP) from severe fever with thrombpcytopenia syndrome virus (SFTSV) or Rift valley fever virus; G protein from Rift valley fever virus, Rabies virus, Ebola viruses, Marburg virus, or human orthopneumovirus; Gn and Gc glycoproteins from Congo hemorrhagic fever virus or Orthohantavirus; L glycoprotein from hepatitis B virus (HBV) and GP120 from human immunodeficiency virus (HIV).

In some embodiments, the recombinant virus has at least one HA and/or NA of Influenza virus expressed thereon.

In other embodiments, the recombinant virus has at least one S or N protein from coronavirus expressed thereon.

In further embodiments, the recombinant virus has at least one glycoprotein of Ebola virus expressed thereon.

In still further embodiments, the recombinant virus has at least one envelop (E) protein of Dengue virus or Zika virus expressed thereon.

According to optional embodiments, the present recombinant virus further comprises a reporter gene encoding a reporter protein that is any of green fluorescence protein (GFP), enhanced green fluorescence protein (EGFP), Discosoma sp. red (DsRed) fluorescent protein, blue fluorescence protein (BFP), enhanced yellow fluorescent proteins (EYFP), tandem dimer Tomato (tdTomato) fluorescent protein, mCherry fluorescent protein, mCitrine fluorescent protein, mCFP fluorescent protein, mPlum fluorescent protein, mVenus fluorescent protein, or mEmerald fluorescent protein.

According to embodiments of the present disclosure, the reporter gene is driven by a second promoter that is the promoter of a gene selected from the group consisting of hr1-hsp70, hsp70, p10, polyhedrin (p-polh), CMV, SV40, RSV, pTriEx, AcMNPV-ie1, WSSV-ie1, gp64, pag, and IRES.

The second aspect of the present disclosure is directed to an insect cell infected by any of the recombinant virus of the present disclosure described above, so that the insect cell has at least one of the exogenous viral protein expressed on its surface.

Examples of insect cell suitable for use in the present disclosure include, but are not limited to, S.furgiperda IPBL-9 (Sf9) cell, Sf21 cell, BmN cells, High Five (Hi5) cell, and Minic Sf9 cell. According to preferred embodiments of the present disclosure, the insect cell is Sf21 cell.

In some embodiments, the insect cell is infected with the recombinant virus having at least one HA and/or NA of Influenza virus expressed thereon, thereby rendering the insect cell to have at least one HA and/or NA of Influenza virus expressed on its surface.

In other embodiments, the insect cell is infected with the recombinant virus having at least one S or N protein from coronavirus expressed thereon, thereby rendering the insect cell to have at least one S or N protein from coronavirus expressed on its surface.

In further embodiments, the insect cell is infected with the recombinant virus having at least one glycoprotein of Ebola virus expressed thereon, thereby rendering the insect cell to have at least one glycoprotein of Ebola virus expressed on its surface.

In still further embodiments, the insect cell is infected with the recombinant virus having at least one envelop (E) protein of Dengue virus or Zika virus expressed thereon, thereby rendering the insect cell to have at least one envelop (E) protein of Dengue virus or Zika virus expressed on its surface.

In some preferred embodiments, the insect cell having at least one viral protein expressed on its surface is isolated from its culture medium, washed and freeze-dried, vacuum-dried, or spray-dried into lyophilized powder.

The third aspect of the present disclosure aims to provide a viral vaccine, which comprises any of the recombinant virus described above.

The fourth aspect of the present disclosure is directed to a method of detecting an antibody of a virus in a biological sample, in which a detection of the antibody in the biological sample indicates that the subject, whom the biological sample derived from, has a viral infection.

The method includes steps of: mixing the biological sample with any of the recombinant virus or the insect cell of the present disclosure; and detecting the antibody captured by any of the recombinant virus or the insect cell of the present disclosure. According to embodiments of the present disclosure, According to preferred embodiment, the insect cell is first treated with a detergent to expose the exogenous viral proteins before mixing with the biological sample.

According to embodiments of the present disclosure, the antibody is an IgA, IgM or IgG.

According to embodiments of the present disclosure, the antibody captured by the recombinant virus of the present disclosure is detected by an enzyme-linked immunosorbent assay (ELISA), hemagglutination (HA) assay, HA inhibition (HI) assay, neuraminidase (NA) assay, NA inhibition (NI) assay, fluorescence-based assay, or flow cytometry screenings.

According to other embodiments of the present disclosure, the antibody captured by the insect cell of the present disclosure is detected by ELISA, HA assay, HI assay, NA assay, NI assay, fluorescence-based assay, flow cytometry screening, syncytium formation, or inhibition of the syncytium formation.

Examples of the biological sample suitable for use in the present method include, but are not limited to, a whole blood sample, a plasma sample, a serum sample, a urine sample, a mucus sample, and purified or filtered forms thereof. Preferably, the biological sample is a serum sample.

According to embodiments of the present disclosure, the virus that may be detected by the present method is a DNA virus, an RNA virus, or a reverse transcribing virus.

The DNA virus may be a species of Adenoviridae, Papillomaviridae.

Polymaviridae, Herpesviridae, Poxviridae, Parvoriridae, Anelloviridae, Circoviridae, or Genomoviridae families.

Exemplary species of Adenoviridae family includes Adenovirus 14.

Exemplary species of Papillomaviridae family includes Human papillomarviruses 16.

Exemplary species of Polymaviridae family includes Simian vacuolating virus 40 (SV40).

Exemplary species of Herpesviridae family includes Epstein-Barr virus (EBV). Exemplary species of Poxviridae family includes Human monkeypox virus.

Exemplary species of Parvoriridae family includes Parvovirus B19.

Exemplary species of Anelloviridae family includes Torque teno virus (TT).

Exemplary species of Circoviridae family includes Porcine circovirus type 2 (PCV2).

Exemplary species of Genomoviridae family includes Gemycircularvirus SL1.

The RNA virus may be a species of Reoviridae, Picobirnaviridae, Picornaviridae, Caliciviridae, Togaviridae, Coronaviridae, Astroviridae, Hepeviridae, Flaviviridae, Arenaviridae, Orthomyxoviridae, Paramyxoviridae, Phenuiviridae, Rhabdoviridae, Filoviridae, Nairoviridae, Pneumoviridae, or Hantaviridae families.

Exemplary species of Reoviridae family includes Rotavirus.

Exemplary species of Picobirnaviridae family includes Human picobirnavirus.

Exemplary species of Picornaviridae family includes Enterovirus 71 (EV71) or Poliovirus.

Exemplary species of Caliciviridae family includes Norwalk virus.

Exemplary species of Togaviridae family includes Chikungunya virus or Rubella virus.

Exemplary species of Coronaviridae family includes, but is not limited to, Severe Acute Respiratory Syndrome coronavirus (SARS-CoV-1), Middle East Respiratory Syndrome coronavirus (MERS-CoV), SARS-CoV-2, Human coronavirus HKU1 HKU1 (HCoV-HUK1), Human coronavirus NL63 (HCoV-NL63), Human coronavirus 229E (HCoV-229E), and Human coronavirus OC43 (HCoV-OC43).

Exemplary species of Astroviridae family includes Astrovirus.

Exemplary species of Hepeviridae family includes Hepatitis E virus.

Exemplary species of Flaviviridae family includes, but is not limited to, dengue virus (DENV), Zika virus, Yellow fever virus (YFV), and Hepatitis C virus.

Exemplary species of Arenaviridae family includes Lassa virus.

Exemplary species of Orthomyxoviridae family includes Influenza virus A, and Influenza virus B.

Exemplary species of Paramyxoviridae family includes Measles virus, Nipah virus, Human parainfluenza virus 3, or Mumps virus.

Exemplary species of Phenuiviridae family includes Severe fever with thrombocytopenia syndrome virus (SFTSV), or Rift Valley fever virus.

Exemplary species of Phabdoviridae family includes Rabies virus.

Exemplary species of Filoviridae family includes Ebola virus (EBOV) or Marburg virus.

Exemplary species of Nairoviridae family includes Congo hemorrhagic fever virus.

Exemplary species of Pneumoviridae family includes Human orthopneumovirus. Exemplary species of Hantaviridae family includes Orthohantavirus.

The reverse transcribing virus is a species of Retroviridae or Hepadnaviridae families.

Exemplary species of Retroviridae family includes Human immunodeficiency virus (HIV).

Exemplary species of Hepadnaviridae family includes Hepatitis B virus.

The fifth aspect of the present disclosure is to provide a method of identifying a drug suitable for the treatment of an infection caused by a virus. The method includes steps of: allowing a candidate drug to contact the recombinant virus or the insect cell of the present disclosure; and detecting binding between the candidate drug and the exogeneous viral protein expressed on the surface of the recombinant virus or the insect cell, in which the binding is an indication that the candidate drug is the drug suitable for the treatment of an infection caused by the virus.

According to embodiments of the present disclosure, the drug is an antibody.

According to embodiments of the present disclosure, the binding between the candidate drug and the recombinant virus is detected by an enzyme-linked immunosorbent assay (ELISA), hemagglutination (HA) assay, HA inhibition (HI) assay, neuraminidase (NA) assay, NA inhibition (NI) assay, fluorescence-based assay, or flow cytometry screening; and the binding between the candidate drug and the insect cell is detected by ELISA, HA assay, HI assay, NA assay, NI assay, fluorescence-based assays, flow cytometry screening, syncytium formation, or inhibition of the syncytium formation.

Examples of the exogenous viral protein expressed on the surface of the recombinant virus or the insect cell of the present disclosure include, but are not limited to, VP1 from adenovirus 14; capsid L1 from human papillomaviruses 16; VP1 from Simian vacuolating virus 40 (SV40); envelope protein from Epstein-Barr virus (EBV) or human monkeypox virus; VP1 or VP2 from parvovirus B19; ORF2 from Torque teno virus (TT); Cap from porcine circovirus type 2 (PCV2); Capsid from Gemycircularvirus SL1; ORF1 coat protein from human picobirnavirus; VP1 from enterovirus 71 (EV71), poliovirus, or Norwalk virus; envelope protein E1 from chikungunya virus or Rubella virus; S or N protein from coronavirus; Capsid protein VP34 from Astrovirus; ORF2 from Hepatitis E virus; E or NS1 proteins from flaviviruses; G protein from Lassa virus; HA or NA from Influenza virus A or Influenza virus B; H protein from Measles virus; G protein from Nipah virus, HN from Human parainfluenza virus 3 or Mumps virus; nucleoprotein (NP) from severe fever with thrombpcytopenia syndrome virus (SFTSV) or Rift valley fever virus; G protein from Rift valley fever virus, Rabies virus, Ebola viruses, Marburg virus, or human orthopneumovirus; Gn and Gc glycoproteins from Congo hemorrhagic fever virus or Orthohantavirus; L glycoprotein from hepatitis B virus (HBV) and GP120 from human immunodeficiency virus (HIV).

A further aspect of the present disclosure is to provide a kit suitable for detecting a virus in a biological sample. The kit includes at least, a reagent for detecting an antibody of the virus present in the biological sample, wherein the reagent comprises the present recombinant virus or the present insect cell; a container for housing the reagent; and a legend associated with the container and indicating how to use the present recombinant virus or the present insect cell to detect the antibody present in the biological sample.

According to preferred embodiments of the present disclosure, the present insect cell exists in the form of a powder.

According to preferred embodiments of the present disclosure, the antibody is an IgM or IgG.

Exemplary biological sample suitable for use in the present method includes, but is not limited to, a whole blood sample, a plasma sample, a serum sample, a urine sample, and a mucus sample. Preferably, the biological sample is a serum sample.

Many of the attendant features and advantages of the present disclosure will become better understood with reference to the following detailed description considered in connection with the accompanying drawings.

BRIEF DESCRIPTION OF THE DRAWINGS

The present description will be better understood from the following detailed description read in light of the accompanying drawings, where.

DESCRIPTION

Figure 1:
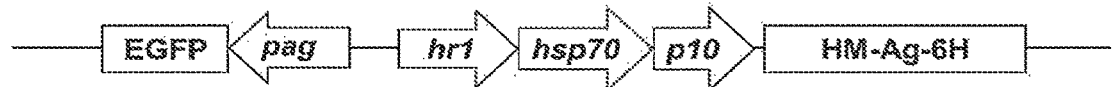
FIG. 1 Schematic representation of baculovirus expression constructs used for displaying different virus antigens. Three expression constructs were used for displaying different virus antigens (Ag) in the present invention. These constructs were driven by a dual promoter containing hr1-hsp70 and p10 promoters (hr1-hsp70-p10) and secreted extracellularly by a honeybee melittin signal peptide (HM). An EGFP driven by a pag promoter was used for each construct as a reporter. (A) Construct 1 for viral antigens with transmembrane domain (TM) at their N-terminus: the antigen-expressing cDNAs locate within a honeybee melittin signal peptide (HM) and a hexameric histidine tag (6H). (B) Construct 2 for viral antigens with TM at their C-terminus: the antigen-expressing cDNAs locate at the C-terminus of HM and 6H. (C) Construct 3 for viral antigens without a TM: the antigen-expressing cDNAs locate at the C-terminus of HM and 6H. A TM and cytoplasmic tail domain (CTD) of GP64 (6MC) is further added to the C-terminus of antigens.
Figure 1:
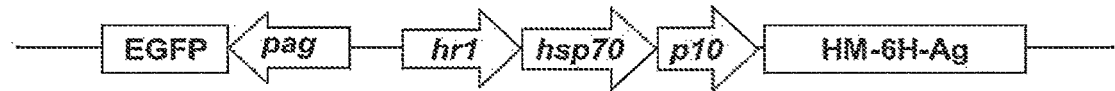
Figure 1:

The detailed description provided below in connection with the appended drawings is intended as a description of the present examples and is not intended to represent the only forms in which the present example may be constructed or utilized. The description sets forth the functions of the example and the sequence of steps for constructing and operating the example. However, the same or equivalent functions and sequences may be accomplished by different examples.

For convenience, certain terms employed in the specification, examples and appended claims are collected here. Unless defined otherwise, all technical and scientific terms used herein have the same meaning as commonly understood by one of the ordinary skill in the art to which this invention belongs.

Provided herein are recombinant viruses, methods, and kits for detecting pathogenic virus infection that requires at least level 3 biocontainment precautions, such as Togaviruses, Flaviviruses, Coronaviruses, Orthomyxoviruses, and etc.

1. Definitions

The term "virus" is used herein to refer to all viruses that directly or indirectly cause disease in humans through direct or indirect contact, particularly the viruses that require at least level 3 biocontainment precautions.

The term "baculoviruses" as used herein refer to arthropod-specific, double-stranded DNA viruses that can be used to control insect pests. The nuclear polyhedrosis viruses ("NPV") are one baculovirus subgroup. Various baculoviruses, including those that infect cotton bollworm, *Helicoverpa zea*, tobacco budworm, *Heliothis virescens*, Douglas fir tussock moth, *Orygia pseudotsugata*, gypsy moth, *Lymantria dispar*, alfalfa looper, *Autographa californica*, European pine sawfly, *Neodiiprion sertifer*, and codling moth, *Cydia pomonella*, are suitable as the vectors for expressing viral proteins of other arthropod born viruses, that is, other than baculoviruses themselves, and preferably those that are regarded as dangerous and lethal arthropod born viruses. In general, baculoviruses with wide host range are preferred, such as *Autographa californica* multiple nucleopolyhedrovirus (AcMNPV). Examples of baculovirus suitable for use in the present invention include, but are not limited to, AcMNPV, *Anagrapha falclfera* MNPV (AfMNPV), *Anticarsia gemmatalis* MNPV (AgMNPV), *Bombyx mori* MNPV (BmMNPV), *Buzura suppressaria* single nucleopolyhedrovirus (BsSNPV), *Helicoverpa armigera* SNPV (HaSNPV), *Helicoverpa zea* SNPV (HzSNPV), *Lymantria dispar* MNPV (LdMNPV), *Orgyia pseudotsugata* MNPV (OpMNPV), *Spodoptera frugiperda* MNPV (SfMNPV), *Spodoptera exigua* MNPV (SeMNPV), and *Trichoplusia ni* MNPVMNPV).

The term "antigen" as used herein is well understood in the art and includes substances which are immunogenic, i.e., immunogens, as well as substances which induce immunological unresponsiveness, i.e., a lack of reactions by the body's defense mechanisms to foreign substances. As used herein, the term "antigen" is intended to mean full length proteins as well as peptide fragments thereof containing or comprising epitope.

The term "transmembrane domain" as used herein is well understood in the art and refers to the amino acid sequence of the protein of a membrane-integrated protein which spans the membrane bilayer.

As used herein, the term "viral vaccine" refers to a recombinant virus, preferably a recombinant baculovirus of the present disclosure, which is characterized in having at least one exogenous viral protein expressed on its surface, thus the recombinant baculovirus per se has the antigenic properties of the viral protein but cannot produce disease.

The term "subject" or "patient" is used interchangeably herein and is intended to mean a mammal including the human species that is susceptible to infection by a virus. The term "mammal" refers to all members of the class Mammalia, including humans, primates, domestic and farm animals, such as rabbit, pig, sheep, and cattle; as well as zoo, sports or pet animals; and rodents, such as mouse and rat. Further, the term "subject" or "patient" intended to refer to both the male and female gender unless one gender is specifically indicated. Accordingly, the term "subject" or "patient" comprises any mammal which may benefit from the treatment method of the present disclosure. Examples of a "subject" or "patient" include, but are not limited to, a human, rat, mouse, guinea pig, monkey, pig, goat, cow, horse, dog, cat, bird, and fowl. In a preferred embodiment, the subject is a human.

The term "biological sample" as used herein refers to a whole blood sample, a plasma sample, a serum sample, a urine sample, and a mucus sample collected from a mammal, which includes human that has or is suspected of having an infection caused by an arthropod born virus. The biological sample can be diluted or undiluted before being subject to the detection of the present recombinant viruses, kits, and/or method. In the case when antibody against the virus are present in the biological sample, the present recombinant virus and/or incent cells present in the kit and/or method will specifically bind with the antibody, thus allow the antibody to be detected by any suitable assay known in the art, which includes but is not limited to, immunogenic assay (e.g., ELISA), hemagglutination (HA) assay, HA inhibition (HI) assay, neuraminidase (NA) assay, NA inhibition (NI) assay, fluorescence-based assay, flow cytometry screening, inhibition of the syncytium formation and etc . . . By contrast, if the antibody against the virus is not present in the biological sample, then the present recombinant viruses and/or insect cells comprised in the present kit and/or method will not bind with the antibody.

The singular forms "a," "and," and "the" are used herein to include plural referents unless the context clearly dictates otherwise. Other than in the operating examples, or where otherwise indicated, all numbers expressing quantities of ingredients, reaction conditions, and so forth used in this application are to be understood as being modified in all instances by the term "about." Accordingly, unless the contrary is indicated, the numerical parameters set forth in this application are approximations that may vary depending upon the desired properties sought to be obtained by the present invention.

2. The Library of Recombinant Viruses Independently Having Viral Antigens Displayed Thereon The present disclosure aims at providing a library of recombinant viruses that serves as antigens for capturing antibodies of a lethal pathogen, particularly the pathogen that requires at least level 2 (e.g., level 3) biocontainment precautions, in a biological sample. By use of the library of recombinant viruses of the present disclosure, the need of expensive level 2 facility, the time-consuming sequencing procedures of the conventional detecting method (e.g., reverse transcription polymerase chain reaction (RT-PCT)) that requires well-trained technician and sophisticated equipment for confirming the identity of the pathogen are eliminated. Most importantly, the library of recombinant viruses of the present disclosure will ensure the first-line operator is free from exposure to highly dangerous pathogens as is common in the existing method for detecting such pathogens. Accordingly, the present library of recombinant viruses offers a safe, fast, easy-to-use, and economically efficient tool for detecting the infection of highly dangerous pathogens. In addition, the detection also serves the purpose of rendering early diagnosis on whether a test subject is infected with such lethal pathogen, so that necessary steps (e.g., medicaments, quarantine and etc) may be timely deployed to treat the subject and to contain the disease or pathogen from spreading.

Accordingly, the first aspect of the present disclosure is directed to a recombinant virus, which is characterized in having at least one viral protein (e.g., a structural protein or a membrane protein) of a pathogenic virus expressed on its surface.

To produce the present recombinant virus, gene cassettes carrying the viral protein(s) of a pathogenic virus of interest are independently constructed and linked to a suitable promoter, so that a viral transfer vector is produced; the transfer vector is then used with the viral DNA to co-transfect a host cell (e.g., an insect cell) to produce the recombinant virus of the present disclosure.

The gene cassette carrying the viral protein of interest is a recombinant virus, which comprises a promoter, and a first nucleic acid encoding the exogenous viral protein operably linked to the promoter. Exemplary promoter suitable for driving exogenous viral gene expression may be the promoter of a gene selected from the group consisting of hr1-hsp70, hsp70, p10, polyhedrin (p-polh), CMV, SV40, RSV, pTriEx, AcMNPV-ie1, WSSV-ie1, gp64, pag, and IRES. In some embodiments, the promoter includes at least, the promoter of p10 gene, and the promoter of hr1-hsp70 gene. In other embodiments, the promoter comprises the promotor of pTriEx gene. In further embodiments, the promoter comprises the promotor of polyhedrin gene (p-polh).

For viral protein that has a transmembrane domain (TM) in its structure, it will automatically anchor on the surface of the recombinant virus after expression. For viral proteins that are not membrane-bound, an additional signal peptide may be added to help transfer the expressed protein product extracellularly; or an anchoring peptide that helps anchoring the expressed protein on the surface membrane of the recombinant virus is added. Accordingly, the recombinant virus may further comprise a second nucleic acid disposed upstream to the first nucleic acid, in which the second nucleic acid encodes a signal peptide, which may be linked to the N-terminus or C-terminus of the viral protein. Exemplary signal peptide suitable for use in the present method may be a honeybee melittin signal peptide (HM/HBM), a GP64 signal peptide (6S), a cecropin B signal peptide, or a GRP78/BiP signal peptide. Optionally, the recombinant virus may further comprise a third nucleic acid encoding a cytoplasmic tail domain (CTD) of a baculovirus glycoprotein GP64 operably linked to the promotor. The CTD of the GP64 will help to anchor the non-membrane-bound viral protein on the surface of the recombinant virus. In some embodiments, the expressed viral protein has the signal peptide HM/HBM linked to its N-terminus. In other embodiments, the expressed viral protein has the signal peptide HM/HBM linked to its N-terminus and the CTD of the GP64 linked to its C-terminus. In further embodiments, the expressed viral protein has the GP64 signal peptide (6S) linked to N-terminus, and the CTD of the GP64 linked to its C-terminus. In still further embodiments, the expressed viral protein has the GP64 signal peptide (6S) and the CTD of the GP64 both linked to its N-terminus.

Additionally, for purification purpose, a hexameric histidine (6H) tag may be added to the expressed viral protein. Accordingly, the recombinant virus may further comprise a fourth nucleic acid disposed upstream or downstream to the first nucleic acid, wherein the fourth nucleic acid encodes a hexameric histidine (6H) tag, which may be linked to the N-terminus or C-terminus of the exogenous viral protein.

Examples of viral vector suitable for use in the present method include, but are not limited to, baculoviral vectors, lentiviral vectors, adenoviral vectors, adeno-associated viral vectors, herpes viral vectors, vaccinia viral vectors, and the like. According to preferred embodiments of the present disclosure, a recombinant baculovirus is constructed to express at least one exogenous viral protein of a pathogen on its surface.

Examples of the exogenous viral protein that may be expressed on the surface of the present recombinant virus include, but are not limited to, VP1 from adenovirus 14; capsid L1 from human papillomaviruses 16; VP1 from Simian vacuolating virus 40 (SV40); envelope protein from Epstein-Barr virus (EBV) or human monkeypox virus; VP1 or VP2 from parvovirus B19; ORF2 from Torque teno virus (TT); Cap from porcine circovirus type 2 (PCV2); Capsid from Gemycircularvirus SL1; ORF1 coat protein from human picobirnavirus; VP1 from enterovirus 71 (EV71), poliovirus, or Norwalk virus; envelope protein E1 from chikungunya virus or Rubella virus; S or N protein from coronavirus; Capsid protein VP34 from Astrovirus; ORF2 from Hepatitis E virus; E or NS1 proteins from flaviviruses; G protein from Lassa virus; HA or NA from Influenza virus A or Influenza virus B; H protein from Measles virus; G protein from Nipah virus, HN from Human parainfluenza virus 3 or Mumps virus; nucleoprotein (NP) from severe fever with thrombpcytopenia syndrome virus (SFTSV) or Rift valley fever virus; G protein from Rift valley fever virus, Rabies virus, Ebola viruses, Marburg virus, or human orthopneumovirus; Gn and Gc glycoproteins from Congo hemorrhagic fever virus or Orthohantavirus; L glycoprotein from hepatitis B virus (HBV) and GP120 from human immunodeficiency virus (HIV). In some embodiments, the recombinant virus has at least one HA and/or NA of Influenza virus expressed on its surface. In other embodiments, the recombinant virus has at least one S or N protein from coronavirus expressed on its surface. In further embodiments, the recombinant virus has at least one glycoprotein of Ebola virus expressed on its surface. In still further embodiments, the recombinant virus has at least one envelop (E) protein of Dengue virus or Zika virus expressed on its surface.

According to preferred embodiments of the present disclosure, the thus produced recombinant baculoviral transfer vector is then co-transfected with a modified AcMNPV viral DNA (FlashBAC™) into an insect host cell. The modified AcMNPV viral DNA provides the necessary viral backbone, which contains the propagation-essential genes. Homologous recombination between the recombinant baculoviral transfer vector and the modified AcMNPV viral DNA in the insect host cell allows the generation of a recombinant baculovirus, which is capable of propagating in the insect host cell and thereby producing the exogenous proteins respectively encoded by the expression gene cassettes (e.g., S or N protein from coronavirus, HA or NA of influenza virus, and etc.). The recombinant baculovirus was further selected and purified, such as by following the expression of a reporter polypeptide. Suitable insect host cell that may be used in the present disclosure includes, but is not limited to, *S. furgiperda* IPBL-9 (Sf9) cell, Sf21 cell, BmN cell, High Five (Hi5) cell, and Minic Sf9 cell. According to preferred embodiments of the present disclosure, the insect host cell is Sf21 cell. Optionally, reporter polypeptides are included in the baculoviral vectors. The expression of the reporter polypeptide may be driven by a promoter selected from the group consisting of hr1-hsp70, hsp70,p10,polyhedrin (p-polh), CMV, SV40,RSV,pTriEx, AcMNPV-ie1, WSSV-ie1, gp64, pag, and IRES. Examples of reporter polypeptide include, but are not limited to, green fluorescence protein (GFP), enhanced green fluorescence protein (EGFP), Discosoma sp. red (DsRed) fluorescent protein, blue fluorescence protein (BFP), enhanced yellow fluorescent proteins (EYFP), tandem dimer Tomato (tdTomato) fluorescent protein, mCherry fluorescent protein, mCitrine fluorescent protein, mCFP fluorescent protein, mPlum fluorescent protein, mVenus fluorescent protein, mEmerald fluorescent protein and etc. In some preferred embodiments of the present disclosure, the reporter polypeptide is EGFP. In other preferred embodiments of the present disclosure, the reporter polypeptide is mCherry fluorescent protein. In further preferred embodiments of the present disclosure, the reporter polypeptide is DsRed. It should be noted that the reporter polypeptide (e.g., EGFP) is not a necessary feature for the aim of this invention.

Accordingly, a library of recombinant viruses may be produced, in which each recombinant virus has at least one exogenous viral protein of interest expressed on its surface. In some embodiments of the present disclosure, a library of recombinant baculoviruses independently having at least one HA or NA of influenza virus expressed thereon is constructed and produced. The library comprising recombinant baculoviruses directed to 18 HA subtypes of influenza A virus and 2 HA subtypes of influenza B viruses is termed "HA-Bacs"; and the library comprising recombinant baculoviruses directed to 11 NA subtypes of influenza A virus is termed "NA-Bacs." In other embodiments, 5 recombinant baculoviruses independently having a glycoprotein (G) subtype of Ebola virus expressed thereon are produced. In further embodiments, recombinant baculoviruses independently having an envelope (E) protein of Dengue virus or Zirka virus expressed thereon are produced.

3. The Library of Insect Cells Independently Having Viral Antigens Displayed Thereon The library of recombinant baculoviruses described above may be used to infect insect cells thereby producing a library of insect cells, in which each insect cell has viral proteins expressed on the surface. In some embodiments, the insect cells are infected with "HA-Bac" thereby producing "HA-cells," in which the insect cells have one of the HA subtypes displayed on their surfaces. In other embodiments, the insect cells are infected with "NA-Bac" thereby producing "NA-cells," in which the insect cells have one of the NA subtypes displayed on their surfaces. In further embodiments, the insect cells are infected with a recombinant baculovirus having a glycoprotein (G) from one out of the five subtypes of Ebola virus expressed thereon, thereby producing insect cells having a glycoptotein subtype of Ebola virus displayed on their surfaces. In still further embodiments, the insect cells are infected with recombinant baculoviruses independently having an envelope (E) protein of Dengue virus or Zirka virus expressed thereon, thereby producing insect cells having envelope (E) protein of Dengue virus or Zirka virus displayed on their surfaces.

According to further embodiments of the present disclosure, the insect cells independently having viral proteins displayed on their surfaces are harvested from the culture media, and freeze-dried, vacuum-dried, or spray-dried into lyophilized powders. The lyophilized insect cells are easy to preserve and transport.

4. Use of the Present Recombinant Virus and/or Insect Cells 4.1 Use of the Present Recombinant Virus and/or Insect Cells to Detect a Virus of Interest The recombinant baculovirus and/or insect cell produced in accordance with the methods described above, in which each recombinant baculovirus or insect cell independently has at least one viral protein of a virus of interest expressed on its surface, accordingly, the entire recombinant baculovirus or the insect cell per se may serve as antigens for capturing antibodies of the interested virus, if any, in a biological sample.

Thus, another aspect of the present disclosure aims at providing a method of detecting the antibody of a virus in a biological sample. The method includes steps of: mixing the biological sample with the present recombinant baculovirus or insect cell; and detecting the antibody against the virus of interest in the biological sample.

In one preferred embodiment, a serum sample of a human subject is mixed with a recombinant baculovirus having a spike protein of SARS-CoV-2 expressed on its surface is used to detect anti-Coronaviridae antibody in the serum sample of the human subject. Accordingly, if the human subject was infected with Coronaviruses, then the antibodies in the serum will bind with the spike protein of the Coronaviruses expressed on the envelope of the recombinant baculovirus, thereby allowing the antibodies to be detected by a suitable assay (e.g., ELISA).

Exemplary assays suitable for detecting the antigen-antibody complex formed in the present method include, but are not limited to, radioimmunoassay, enzyme-linked immunosorbent assay (ELISA), "sandwich" immunoassay, in situ immunoassays (e.g., using colloidal gold, enzyme or radioisotope labels), dot blot, agglutination assay (e.g., gel agglutination assay, hemagglutination (HA) assay, HA inhibition (HI) assay and etc), complement fixation assay, immunofluorescence assay, and immunoelectrophoresis assay, neuraminidase (NA) assay, NA inhibition (NI) assay, flow cytometry screening, syncytium formation, or inhibition of the syncytium formation, and etc. In one embodiment, antibody binding is detected by use of ELISA. In another embodiment, antibody binding is detected by use of HA assay. In one embodiment, the antibody comprises an immunoglobulin M (IgM). In another embodiment, the antibody comprises an immunoglobulin G (IgG).

According to embodiments of the present disclosure, antibodies are detected in bodily fluids, including but are not limited to whole blood, serum, plasma, mucus, urine, and purified or filtered forms thereof. In one preferred example, antibodies were detected from a serum sample. In other embodiments, antibodies are detected from a plasma sample.

The present method is particularly suitable for detecting antibodies of viruses that require at least level 2 biocontainment precautions. The virus may be a DNA virus, an RNA virus, or a reverse transcribing virus.

The DNA virus may be a species of Adenoviridae, Papillomaviridae, Polymaviridae, Herpesviridae, Poxviridae, Parvoriridae, Anelloviridae, Circoviridae, or Genomoviridae families.

Exemplary species of Adenoviridae family includes Adenovirus 14.

Exemplary species of Papillomaviridae family includes Human papillomarviruses 16.

Exemplary species of Polymaviridae family includes Simian vacuolating virus 40 (SV40).

Exemplary species of Herpesviridae family includes Epstein-Barr virus (EBV). Exemplary species of Poxviridae family includes Human monkeypox virus.

Exemplary species of Parvoriridae family includes Parvovirus B19.

Exemplary species of Anelloviridae family includes Torque teno virus (TT).

Exemplary species of Circoviridae family includes Porcine circovirus type 2 (PCV2).

Exemplary species of Genomoviridae family includes Gemycircularvirus SL1.

The RNA virus may be a species of Reoviridae, Picobirnaviridae, Picornaviridae, Caliciviridae, Togaviridae, Coronaviridae, Astroviridae, Hepeviridae, Flaviviridae, Arenaviridae, Orthomyxoviridae, Paramyxoviridae, Phenuiviridae, Rhabdoviridae, Filoviridae, Nairoviridae, Pneumoviridae, or Hantaviridae families.

Exemplary species of Reoviridae family includes Rotavirus.

Exemplary species of Picobirnaviridae family includes Human picobirnavirus.

Exemplary species of Picornaviridae family includes Enterovirus 71 (EV71) or Poliovirus.

Exemplary species of Caliciviridae family includes Norwalk virus.

Exemplary species of Togaviridae family includes Chikungunya virus or Rubella virus.

Exemplary species of Coronaviridae family includes, but is not limited to, Severe Acute Respiratory Syndrome coronavirus (SARS-CoV-1), Middle East Respiratory Syndrome coronavirus (MERS-CoV), SARS-CoV-2, Human coronavirus HKU1 HKU1 (HCoV-HUK1), Human coronavirus NL63 (HCoV-NL63), Human coronavirus 229E (HCoV-229E), and Human coronavirus OC43 (HCoV-OC43).

Exemplary species of Astroviridae family includes Astrovirus.

Exemplary species of Hepeviridae family includes Hepatitis E virus.

Exemplary species of Flaviviridae family includes, but is not limited to, dengue virus (DENV), Zika virus, Yellow fever virus (YFV), and Hepatitis C virus.

Exemplary species of Arenaviridae family includes Lassa virus.

Exemplary species of Orthomyxoviridae family includes Influenza virus A, and Influenza virus B.

Exemplary species of Paramyxoviridae family includes Measles virus, Nipah virus, Human parainfluenza virus 3, or Mumps virus.

Exemplary species of Phenuiviridae family includes Severe fever with thrombocytopenia syndrome virus (SFTSV), or Rift Valley fever virus.

Exemplary species of Phabdoviridae family includes Rabies virus.

Exemplary species of Filoviridae family includes Ebola virus (EBOV) or Marburg virus.

Exemplary species of Nairoviridae family includes Congo hemorrhagic fever virus.

Exemplary species of Pneumoviridae family includes Human orthopneumovirus. Exemplary species of Hantaviridae family includes Orthohantavirus.

The reverse transcribing virus may be a species of Retroviridae or Hepadnaviridae families.

Exemplary species of Retroviridae family includes Human immunodeficiency virus (HIV).

Exemplary species of Hepadnaviridae family includes Hepatitis B virus.

4.2 Use of the Present Recombinant Virus and/or Insect Cells to Identify Candidate Drugs The recombinant baculoviruses and/or insect cells produced in accordance with the methods described above, in which each recombinant baculovirus or insect cell independently has at least one viral protein of a pathogenic virus expressed on its surface, accordingly, the entire recombinant baculovirus or the insect cell per se may serve as agents for identifying drugs suitable for the development of a medicament for treating an infection caused by the pathogenic virus.

Thus, another aspect of the present disclosure aims at providing a method of identifying a candidate drug that binds to the viral protein(s) displayed on the surface of the present recombinant baculovirus and/or insect cell. The method includes steps of: allowing the candidate drug to contact the recombinant virus or the insect cell of the present disclosure; and detecting a binding between the candidate drug and the viral protein(s) expressed on the surface of the recombinant virus or the insect cell, in which the binding is an indication that the candidate drug is the drug suitable for the treatment of an infection caused by the pathogenic virus.

According to embodiments of the present disclosure, the drug is an antibody.

According to embodiments of the present disclosure, the binding between the candidate drug and the recombinant virus and/or insect cell is detected by radioimmunoassay, enzyme-linked immunosorbent assay (ELISA), "sandwich" immunoassay, in situ immunoassays (e.g., using colloidal gold, enzyme or radioisotope labels), dot blot, agglutination assay (e.g., gel agglutination assay, hemagglutination (HA) assay, HA inhibition (HI) assay and etc), complement fixation assay, immunofluorescence assay, and immunoelectrophoresis assay, neuraminidase (NA) assay, NA inhibition (NI) assay, flow cytometry screening, syncytium formation, or inhibition of the syncytium formation, and etc. In one embodiment, the binding is detected by use of ELISA. In another embodiment, the binding is detected by use of HA assay.

Examples of the exogenous viral protein expressed on the surface of the recombinant virus or the insect cell of the present disclosure include, but are not limited to, VP1 from adenovirus 14; capsid L1 from human papillomaviruses 16; VP1 from Simian vacuolating virus 40 (SV40); envelope protein from Epstein-Barr virus (EBV) or human monkeypox virus; VP1 or VP2 from parvovirus B19; ORF2 from Torque teno virus (TT); Cap from porcine circovirus type 2 (PCV2); Capsid from Gemycircularvirus SL1; ORF1 coat protein from human picobirnavirus; VP1 from enterovirus 71 (EV71), poliovirus, or Norwalk virus; envelope protein E1 from chikungunya virus or Rubella virus; S or N protein from coronavirus; Capsid protein VP34 from Astrovirus;

ORF2 from Hepatitis E virus; E or NS1 proteins from flaviviruses; G protein from Lassa virus; HA or NA from Influenza virus A or Influenza virus B; H protein from Measles virus; G protein from Nipah virus, HN from Human parainfluenza virus 3 or Mumps virus; nucleoprotein (NP) from severe fever with thrombpcytopenia syndrome virus (SFTSV) or Rift valley fever virus; G protein from Rift valley fever virus, Rabies virus, Ebola viruses, Marburg virus, or human orthopneumovirus; Gn and Gc glycoproteins from Congo hemorrhagic fever virus or Orthohantavirus; L glycoprotein from hepatitis B virus (HBV) and GP120 from human immunodeficiency virus (HIV).

According to embodiments of the present disclosure, the candidate drug identified by the present method could bind with the viral protein(s) described above, which is an indication that the identified candidate drug may be useful for the development of a medicament suitable for the treatment of an infection caused by the virus that the viral protein derived from.

4.3 Use of the Present Recombinant Virus as Vaccines

As the viral proteins expressed on the present recombinant baculovirus are primary viral components that give rise to protect immune response in a live subject (e.g., a human), accordingly, the present recombinant baculovirus may also serve as a vaccine to immunize its recipient (i.e., prevent the recipient from being infected by pathogenic viruses).

To this purpose, the present recombinant baculoviruses having desired viral proteins (e.g., influenza HA or NA) expressed thereon may be used as vaccines and stored at proper condition without losing their immunization activities.

According to preferred embodiments of the present disclosure, the present recombinant baculoviruses independently having HA7 or NA9 of influenza A virus expressed on their surfaces are used as vaccines to protect its recipient against influenza H7N9 infection. Subjects immunized with the present vaccines (i.e., the present recombinant baculoviruses independently having HA7 or NA9 of influenza A virus expressed on their envelopes) all remain healthy and alive after the infection of influenza H7N9 viruses, compared to those of the control subjects (i.e., immunized with phosphate-buffered saline or wild-typed baculovirus), in which all of the control subjects were found dead 6 days after the infection.

5. Kits for Detecting a Virus of Interest

To provide those skilled in the art tools to use the present invention, the recombinant baculovirus and/or insect cells of the present disclosure are assembled into kits for the diagnosis, detection, or confirmation of the virus of interest. In preferred embodiments, the presence of antibodies reactive to the recombinant baculovirus and/or insect cells of the present disclosure is used to provide a diagnosis to a subject. For example, the detection of high levels of antibodies reactive to the recombinant baculovirus and/or insect cells of the present disclosure, as compared to controls, in a sample, is an indication of infection of the virus of interest. The information provided is also used to direct the course of treatment or necessary quarantine means to prevent the disease or the virus from spreading. For example, if a subject is found to have antibodies against the recombinant baculovirus of the present disclosure, therapies for the treatment of the disease caused by the virus may be started at an earlier time when they are more likely to be effective, while necessary steps to contain the virus from spreading may also be conducted at the same time.

In one embodiment, the present invention provides a kit for detecting and/or diagnosis a virus of interest (e.g., influenza A virus, coronavirus, Ebola virus, and etc) by use of the present recombinant baculoviruses and/or insect cells. The components included in the kits are: a container, reagents for detecting an antibody in a biological sample, wherein the reagents comprise the present recombinant baculoviruses and/or insect cells produced in accordance with the procedure described in embodiments of this invention, the recombinant baculoviruses or insect cells independently has at least one viral protein of a virus of interest expressed on its surface; and a legend associated with the container and indicating how to use the recombinant baculoviruses and/or insect cells for detecting the antibody in a biological sample. The legend may be in a form of pamphlet, CD, VCD or DVD. The kit may further comprise a negative control that indicates the normal level of the antibody that binds with the recombinant baculoviruses and/or insect cells in a healthy subject.

The following examples are provided to illustrate the present invention without, however, limiting the same thereto.

EXAMPLES

Material and Methods
Cells and Media

*Spodoptera frugiperda* IPLB-Sf21 (Sf21) cells were cultured at 26° C. in TC100 insect medium (Gibco, Thermo Fisher Scientific) with 10% fetal bovine serum (FBS). *Bombyx mori* BmN cells were also cultured at 26° C. but in TC100 insect medium with 15% fetal bovine serum (FBS). *Trichoplusia ni* BTI-TN-5B1-4 (Hi5) cells were cultured at 26° C. in ESF 921 serum-free insect cell culture medium (Expression Systems) without adding FBS. Madin-Darby canine kidney (MDCK) cells were cultured at 37° C. and 5% CO2 using Dulbecco's Modified Eagle's medium (DMEM) (Sigma, St. Louis, MO) with 10% FBS. The A549 cells (ATCC: CCL-185) were cultured at 37° C. and 5% CO2 using F-12K medium (Gibco, Thermo Fisher Scientific) with 10% FBS.

Construction of Recombinant Baculoviruses cDNAs encoding viral antigens were synthesized or purchased from Sino Biological Inc., China. The transfer vector pABpaR2pol was constructed by inserting a DsRed2 reporter gene driven by pag promoter (p-pag) into the EcoRV restriction enzyme site of pBacPAK8 (Clontech Laboratories, Inc.). The transfer vector pABEGhhp10 was constructed by replacing the DsRed2 reporter gene with EGFP gene and replacing the polyhedrin promoter (p-polh) of multiple cloning sites with the dual promoter containing hr1-hsp70 and p10 promoters (hr1-hsp70-p10). The transfer vector pTriEx4-SV40-pag-mCherry was constructed by inserting an mCherry repoter gene driven by the dual promoter containing SV40 and pag promoters (SV40-pag). Three strategies were used to express viral antigens with different features. Construct 1 was used to display membrane proteins with TM at the N-terminus, in which the antigens were fused with an N-terminal honeybee melittin signal peptide (HM) and a C-terminal hexameric histidine tag (6H) (FIG. 1, panel (A)). Construct 2 was used to display membrane proteins with TM at the C-terminus, in which the antigens were fused with N-terminal HM and 6H (FIG. 1, panel (B)). Construct 3 was used to display non-membrane-bound proteins, in which the antigens were fused with N-terminal HM and 6H (FIG. 1, panel (C)). Heterologous™ and cytoplasmic tail domain (CTD) from baculovirus major glycoprotein GP64 (6MC) were further fused to the C-terminus of antigens of Construct 3. All the fragments were amplified by PCR and then ligated by In-Fusion HD Cloning Kit (Clontech Laboratories, Inc.). The nucleotide sequences of the plasmids and the orientation of the inserted fragments were verified by DNA sequencing. For transient expression of HA7 and NA9 in A549, pTriEx3-HA7 and pTriEx3-NA9 were cloned by inserting the cDNAs of HA and NA from H7N9 (A/Anhui/1.2013) into the expression vector pTriEx3 (Clontech).

Recombinant AcMNPVs were generated by co-transfecting the transfer vector plasmids with FlashBAC™ (Mirus, a modified AcMNPV baculovirus genome) into Sf21 cells by Cellfectin (Life Technologies). The resulting recombinant baculoviruses were propagated in Sf21 and isolated through end-point dilutions. The expression of DsRed2 or EGFP reporter was used to monitor the proper baculovirus infection in cells.

Confocal Microscopy

Sf21 cells ($1 \times 10^4$) were seeded into 8-well Millicell® EZ slides (Millipore) and the cells were infected with recombinant baculovirus using an MOI=5. Two days after infection, the cells were fixed with 4% paraformaldehyde for 15 minutes at room temperature. After blocking with 3% Bovine Serum Albumin (BSA) in DPBS for 1 h at room temperature, the cells were incubated with mouse anti-His-tagged antibody (1:5000, GeneTex GTX628914) overnight at 4° C. The cells were washed three times with DPBST (DPBS, plus 0.1% Tween 20) and incubated with 1:200-diluted Alexa Fluor 488 goat anti-mouse IgG secondary antibody (Invitrogen) for 1 h at room temperature. Images were obtained with a Zeiss laser confocal microscope (LSM780) and analyzed by ZEN 2010 software (Zeiss). For observing syncytium formation induced by E proteins, Sf21 cells were infected with E-Bac at an MOI=10. The syncytium formations were observed at 3 d.p.i by Confocal microscopy.

Purification of Recombinant Baculoviruses

The recombinant baculoviruses were propagated by infecting Sf21 cells at MOI of 0.1 and harvested 5 days after infection. For large-scale production of baculovirus, cells were cultured and infected in a 500-ml Corning disposable spinner bottle (Corning). Viral supernatants were purified by one round of sucrose gradient ultracentrifugation, followed by a sucrose cushion ultracentrifugation.

Immunogold Electron Microscope

Ten µl of purified baculovirus particle solutions were adsorbed on carbon-coated grids for 3 min. After removing the excess, the grids were blocked with 2% BSA, washed 3 times with PBS for 5 minutes, and then exposed to anti-His$_6$ mAb (1:100 dilution) for 30 min. After two PBS washes, the grids were exposed to anti-mouse IgG conjugated with 6-nm gold particles (1:50 dilution, Sigma) for 30 minutes. After three more PBS washes, the grids were negatively stained with 2% phosphor tungstic acid (Sigma) for 2 min, air-dried, and examined under the transmission electron microscope.

Hemagglutination Assay

For determining the activity of HA displayed on HA-cells, the infected insect cells were collected from the monolayer cultures and centrifuged to remove the culture medium. The pelleted cells were suspended in PBS (pH 7.2) plus 0.01% BSA. Fifty µl of the cell suspension was added into the V-bottom 96-well plates and serially diluted 2-fold. For determining the activity of HA displayed on HA-bacs, the 50-1 cell suspension was replaced by 50 µl of virus supernatants. Fifty µl of 1% turkey erythrocytes (suspended in PBS+0.01% BSA) were added into each well and incubated for 1 h at room temperature. The hemagglutination titer was defined as the reciprocal of the highest dilution to agglutinate turkey erythrocytes.

NA Activity and NA Inhibition (NI) Assays

NA activity and NI assays were performed using MUNANA assay.

MUNANA assay is based on the cleavage of a fluorescent substrate, 2'-(4-methylumbelliferyl)-$\alpha$-D-N-acetyl-neuraminic acid sodium salt hydrate (4-MUNANA; Sigma-Aldrich, Cat: M8639) by influenza NA; and the yield of free 4-methylumbelliferone (4-MU) fluorescent product is then quantitated based on its fluorescence intensity. In the NA assay, NA-Bacs or NA-cells were two-fold serial diluted (with a volume of 20 l) in 96-well opaque black flat-bottom microplates (Corning Inc., Corning, NY) using 1× NA-Flour Assay buffer (33 mM MES, 4 mM CaCl$_2$). Thirty μl of 4-MUNANA substrate (final concentration of 100 μM) was added into each in 96-well plates and mixed well by pipetting. Samples in 96-well plate were then incubated at 37° C. for 1 h to catalyze the 4-MUNANA substrate. The reaction was terminated by adding 150 μl of stop solution (0.14 M NaOH in 83% ethanol). The fluorescence due to release of 4-MU was read using an excitation wavelength of 365 nm and an emission wavelength of 450 nm. In the NI assay, NA inhibitors (Oseltamivir or Zanamivir) were two-fold serial diluted to a final volume of 10 μl, then added to NA-Bacs or NA-cells (volume: 10 μl) and incubated at 37° C. for 30 min before adding the 4-MUNANA substrate.

Cell-Based ELISA

Sf21 cells, BmN cells, or Hi5 cells were infected with recombinant baculoviruses to display each antigen on cell surfaces. Culture medium was removed at 3 d.p.i and the cells were washed once by DPBS. The cells were seeded into wells of 96-well plate and then fixed by 4% paraformaldehyde. For transient expression of HA7 and NA9 in A549 cells, the plasmids pTriEx3-HA7 and pTriEx3-NA9 were transfected into A549 cells using TransLT transfection reagent (Mirus) following the manufacturer's protocol. Two days after the transfection, the cells were fixed with 4% paraformaldehyde.

After fixation, the cells could be lyophilized by removing the supernatant and placing the plates in a freeze drier for 2 h. To start the ELISA, the cells were incubated with blocking buffer (3% BSA in DPBS) for 1 h at room temperature. The primary antibody was diluted in blocking buffer and added to the cell samples and incubated for 1 h at room temperature or overnight at 4° C. After three washes with 0.1% Tween 20 in PBS (PBST), horseradish peroxidase (HRP)-conjugated secondary antibody was added to each well for 1 h at room temperate. If the serum samples were applied in the assay, the blocking buffer, sample dilution buffer, and secondary antibody dilution buffer were replaced by those of Chon-Block™ (Chondrex, Inc.) according to the manufacturer's protocol.

After the incubation of secondary antibodies, the samples were washed three times with PBST and the 3, 3', 5, 5'-tetramethylbenzidine (TMB) substrate was then added. Coloring reactions were stopped using 2M sulfuric acid and ELISA absorbance was measured at 450 nm.

Hemagglutination Inhibition (HI) Assays

Antibodies or serum samples were serially diluted 2-fold in v-bottom 96-well plates (final volume: 25 μl). Eight HA units of HA7-Bac with a volume of 25 μl were added to each well. The plates were covered and incubated at room temperature for 30 min. Fifty μl of freshly prepared 1% turkey red blood cells (in PBS) was added to each well. The plates were left to stand at 25° C. for 30 min or 1 h. The HAI titer was determined by the reciprocal of the highest dilution containing non-agglutinated red blood cells. Positive and negative serum or antibody controls were included on each plate. If HAI assays were performed on serum samples, the serum samples were treated with a receptor-destroying enzyme (RED: Denka Seiken Co., Japan) at 37° C. overnight and heat-inactivated at 56° C. for 30 min before the assays to inactive non-specific inhibitors.

Generation of mAbs

Six- to 8-week-old inbred female BALB/c mice were used. Mice (n=5) were immunized intraperitoneally with $10^9$ pfu of purified HA7-Bac or NA9-Bac. Two booster shots were administered 2 and 4 weeks after the primary immunization. One week after the final immunization, sera were collected from the immunized mice to determine the anti-HA and anti-NA antibody contents (by ELISA). Two weeks after the final immunization, splenocytes were collected from the mice and fused with mouse myeloma cells to produce the hybridoma cells. The successful hybridoma cells were selected by growing the hybrid cells in HAT selection media (Sigma-Aldrich Inc., St. Louis, USA). Single hybridoma clones were isolated by 2-3 rounds of limiting dilution method. Hybridoma clones secreting HA7- or NA9-mAbs were identified by applying the culture supernatants to cell-Based ELISA displaying HA7 or NA9.

Microneutralization Assay

The A/Taiwan/01/2013 (H7N9) influenza virus was amplified and its 50% tissue culture infective dose (TCID$_{50}$) was determined in MDCK cells. HA7-Bac derived mAbs were serially diluted 2-fold (from 1:2) and mixed with 10 TCID$_{50}$ of H7N9 virus. The mixtures were incubated at 4° C. for 1 h and then transferred to monolayer MDCK cells in 96-well plates. After the culture at 37° C., the neutralizing of HA7-Bac derived mAbs were determined at 3 d.p.i. The reciprocal of the highest dilution that completely prevented the cytopathic effect was defined as the neutralizing titer. Each mAb was assayed at least in triplicate.

Enzyme-Linked Lectin Assay (ELLA)

NA9-Bac derived mAbs were serial ten-fold diluted and mixed with $10^7$ pfu of NA9-Bac individually. The mixtures were transferred to 96-well plates coated with fetuin and incubated for 16-18 h. After incubation, horseradish peroxidase-labeled peanut agglutinin was added to bind the exposed galactose. TMB substrate was added 2 hours after to determine the enzymatic cleavage of fetuin by NA proteins of NA9-Bac. The percent inhibition of NA enzymatic activity of each mAb was calculated by comparing the values to NA9-Bac control (NA9-Bac virus mixed with Control IgG).

Vaccination Studies in Mice

Six-week-old female BALB/c mice (n=5 per group) were immunized intraperitoneally with $10^9$ pfu of HA7-Bac, NA9-Bac, or wt-Bac directly without the adding of adjuvant. Mice of the positive control group received the injection of 10 μg HA7 purified protein homogenized with Freund's complete adjuvant. Mice of the negative control group were injected with PBS only. Two boost shots were administered 2 and 4 weeks after the primary immunization. In the boost shots, the 10-ug HA7 purified protein antigen of the positive control group was mixed with Freund's incomplete adjuvant instead. Two weeks after the final immunization, all the mice were challenged with 10 MLD$_{50}$ of A/Taiwan/01/2013 H7N9 influenza viruses. Mice were monitored daily for survival and weight changes.

Example 1 Construction of Recombinant
Baculoviruses Displaying Viral Antigens

Viral antigens were classified into three different forms: (1) the membrane proteins with transmembrane domain (TM) at the N-terminus, (2) the membrane proteins with TM at the C-terminus, and (3) non-membrane-bound proteins. For viral proteins belonging to form (1), they were expressed using Construct 1 (FIG. 1, panel (A)) in which a honeybee melittin signal peptide (HM) was added to the N-terminus and a hexameric histidine tag (6H) was added to the C-terminus of the antigen. For the form 2 viral antigens, they were expressed by Construct 2 (FIG. 1, panel (B)), in which both HM and 6H were added to the N-terminus of the antigen. For the form 3 viral antigens, they were expressed by Construct 3 (FIG. 1, panel C)), in which the HM and 6H were both added to the N-terminus of the antigen, and the TM and cytoplasmic tail domain (CTD) of baculovirus major glycoprotein GP64 (6MC) were added to the C-terminus of the antigen. By adding the HM, the protein products were able to be transferred extracellularly. In Constructs 1 or 2, the antigens would anchor on the membrane of insect cells or baculovirus by their own TM. In Construct 3, the antigens would anchor on the membrane by the added 6MC.

Figure 2:
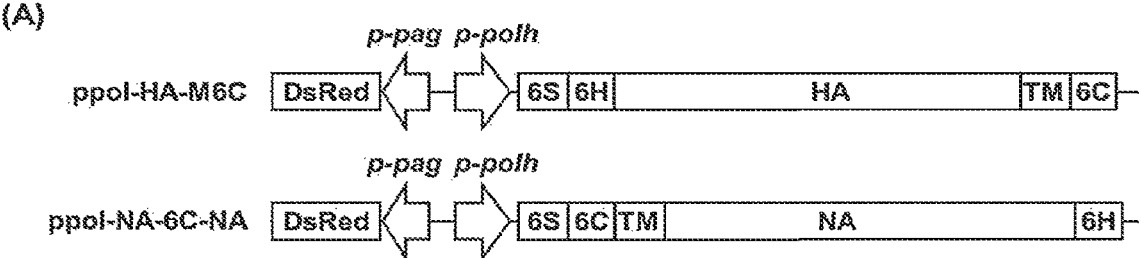
FIG. 2 Schematic representation of baculovirus expression constructs used for displaying influenza HA and NA. Two sets of expression constructs were used for displaying influenza HA and NA. (A) pABpaR2pol group: HA or NA retains its TM and fuses with GP64 CTD (6C). Gene of interest was driven by the polyhedrin promoter (p-polh), secreted extracellularly by GP64 signal peptide (6S) and labeled with a histidine tag (6H). The construct included a pag promoter (p-pag) that drove the DsRed gene as a reporter. (B) pABEGhhp10 group: the TM of HA was replaced with GP64 TM (6M) followed by the GP64 CTD (6C). The construct was driven by the dual promoter containing hr1-hsp70 and p10 promoters (hr1-hsp70-p10) and secreted extracellularly by a honeybee melittin signal peptide (HM). An EGFP driven by pag promoter was used as a reporter.
Figure 2:
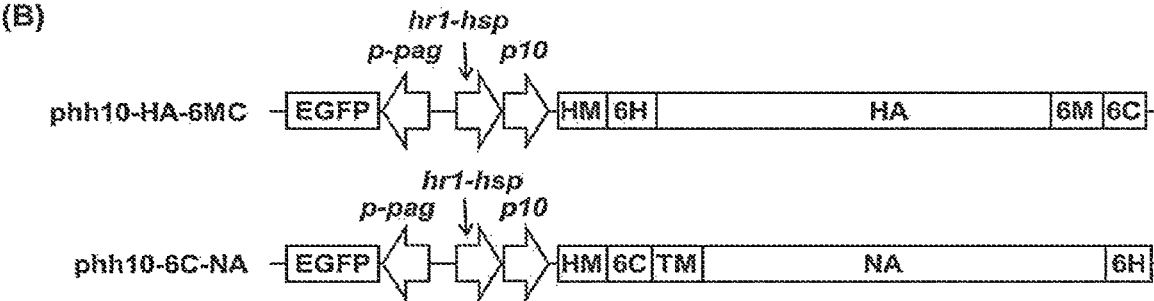
Figure 3:
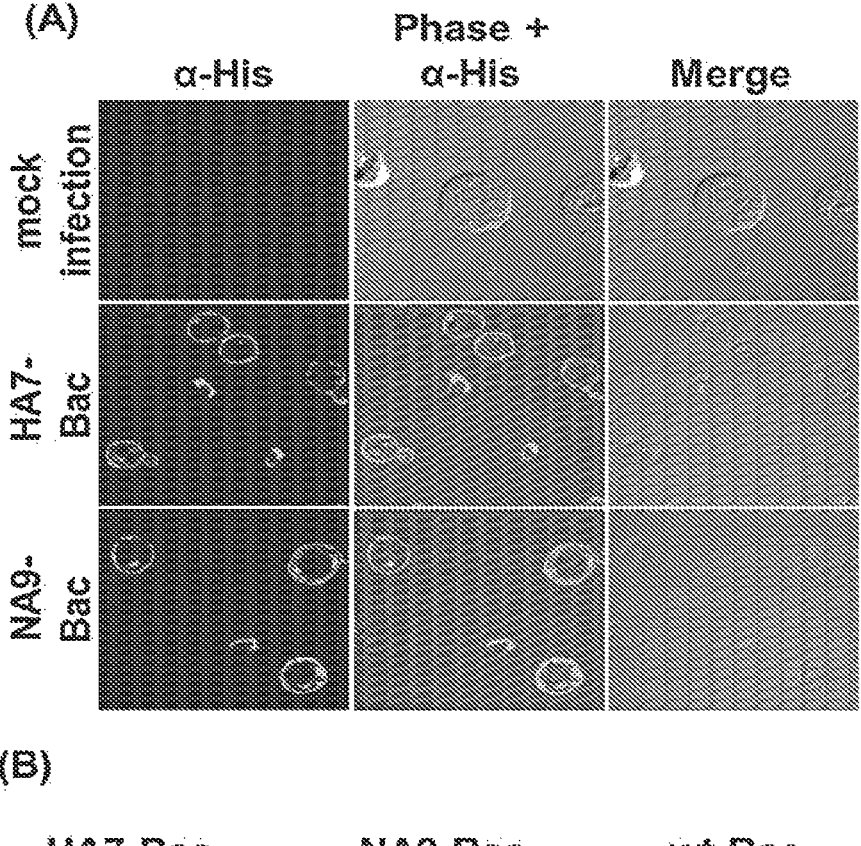
FIG. 3 Display of HA7 and NA9 on the surface of insect cells and purified baculovirus. (A) Immunofluorescence staining determining the surface display of HA7 and NA9 on the membrane of insect cells. Insect Sf21 cells infected with HA7-Bac and NA9-Bac were stained by primary anti-His antibody and secondary Alexa Fluor 488 antibody. The non-infected cells served as mock infection control. (B) Immunogold electron micrographs showing the surface incorporation of HA7 and NA9 on the baculovirus envelopes. The Sf21 cells were infected with HA7-Bac or NA9-Bac at an MOI=0.1. The supernatants were harvested at 5 d.p.i, and the virions were purified by sucrose gradient ultracentrifugation. The recombinant HA7 and NA9 were labeled by primary anti-His antibody and secondary anti-mouse IgG antibody conjugated with 6-nm gold particles.
Figure 3:
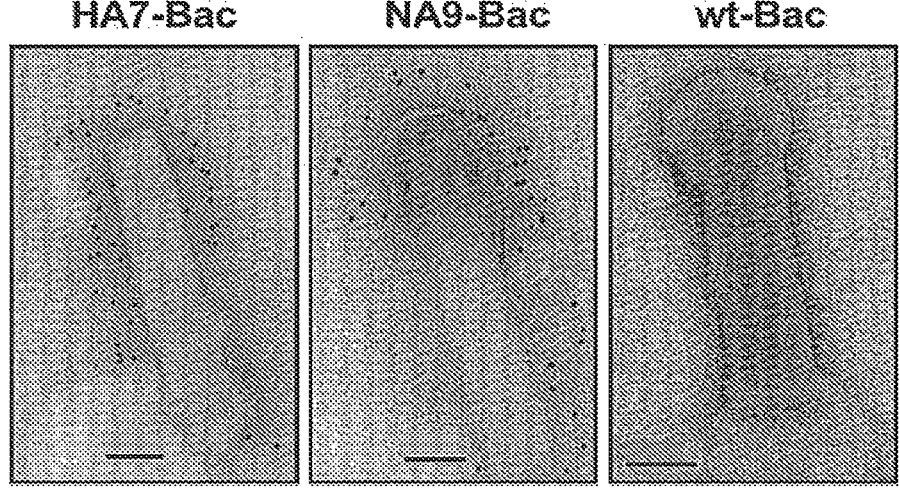

In most of the embodiments. The expression was driven by a dual promoter, which included hrl-hsp70 and p10 promoters (i.e., hrl-hsp70-p10). In other embodiments, a polyhedrin promoter (p-polh) (FIG. 2, panel (A)) or a pTriEx promoter was used (FIG. 3) to replace the dual promoter (i.e., hrl-hsp70-p10). Further, the HM signal peptide could also be replaced by the GP64 signal peptide (6S in FIG. 2, panel (A)). Different reporter genes could also be used, including DsRed (FIG. 2, panel (A)), mCherry (FIG. 3), and EGFP (FIG. 2, panel (B)).

Example 2 Recombinant Baculovirus Displaying Influenza HA or NA

In this example, recombinant baculoviruses having the HA from 18 identified HA influenza A subtypes (i.e., H1-H18) and 2 influenza B lineages (i.e., Yamagata and Victoria) were expressed (Table 1); as well as recombinant baculoviruses having 11 NA subtypes of influenza A viruses and 1 NA subtypes of influenza B viruses were also expressed (Table 2). The HA-Bac and NA-Bac were independently constructed using the construct depicted in FIG. 2, in which the influenza HA was expressed using Construct 3 as described in Example 1 (FIG. 2, panel (B)). Additionally, for some antigens of form 1, such as the influenza NA, the CTD was replaced by that from GP64 (6C) (FIG. 2, panel (A) and (B)).

Figure 16:
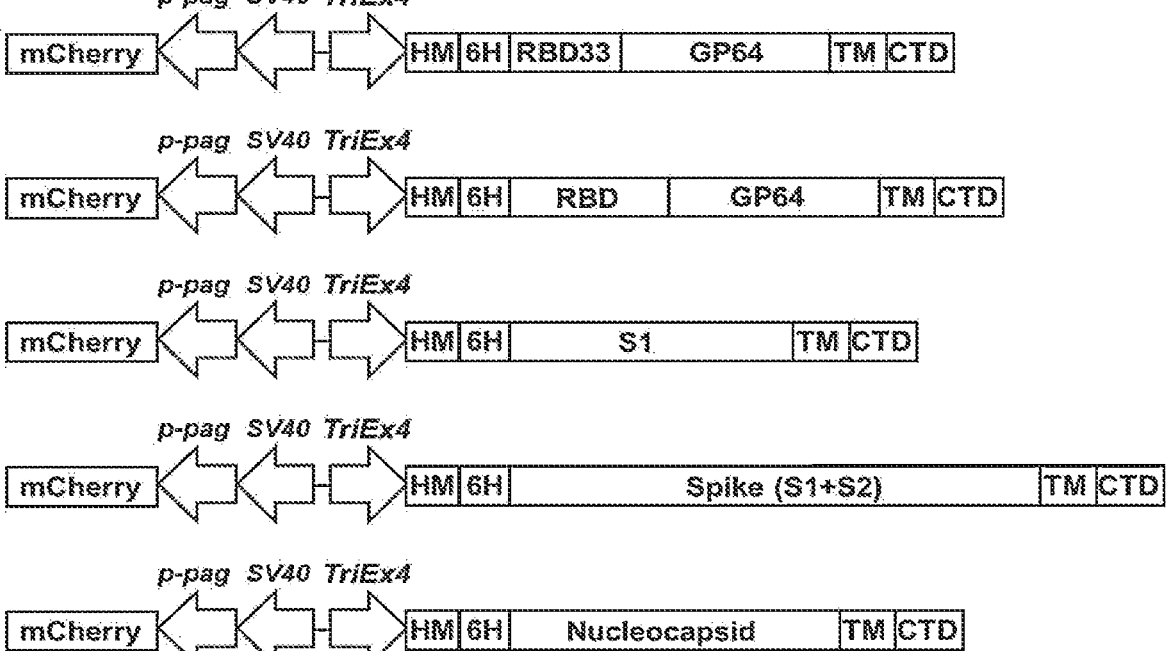
FIG. 16 Baculovirus expression construct used for displaying N or S proteins of SARS-CoV-2. The expression constructs pTriEx-HM-6H-CoV-2-N-6MC and pTriEx-HM-6H-CoV-2-S-6MC were used to generate N-Bac and S-Bac baculoviruses, respectively. Numbers indicate amino acid boundaries of N and S from the original sequence. mCherry: mCherry fluorescent protein; pag: pag promoter; SV40: SV40 promoter; pTriEX: pTriEX4 promoter; HM: honeybee melittin signal peptide; 6H: histidine tag; TM: transmembrane domain; CTD: cytoplasmic tailed domain.

For the dominant human-infectious influenza viruses, such as H1N1 and H3N2, HAs or NAs from different virus isolates were further added to achieve better coverage (Tables 1 and 2). Similarly, for Ebola viruses, five strains that have infected humans and caused the epidemics, i.e., Zaire, Sudan, Taï forest, Reston, and Bundibugyo, were also constructed. For specific purposes, viruses displaying the subunits of a heterologous antigen, i.e., the fragmented of full-length Spike (S) or Nucleocapsid (N) protein from SARS-CoV-2, were also constructed (FIG. 16).

TABLE 1

| HA strains used to construct the HA-Bac. | |
| --- | --- |
| HA subtypes | Influenza virus strain |
| H1 | A/Mexico City/003/2009 (HIN1) |
| H2 | A/Japan/305/1957 (H2N2) |
| H3 | A/Hong Kong/1-1-MA-12/1968 (H3N2) |

TABLE 1-continued

| HA strains used to construct the HA-Bac. | |
| --- | --- |
| HA subtypes | Influenza virus strain |
| H3 | A/Switzerland/97 15293/2013 (H3N2) |
| H3 | A/Hong Kong 480/2014 (H3N2) |
| H4 | A/duck/Czech/1956 (H4N6) |
| H5 | A/d uck/Chma/E319-2/03 (H5N1) |
| H5 | A/chicken/Tai wan/1209/2003 (Highly Pathogenic H5N2) |
| H6 | A/turkey/Massachusetts/3740/1965 (H6N2) |
| H7 | A/duck/Anhui/SC702/2013 (H7N9) |
| H8 | A/turkey/Ontario/6118/1968 (H8N4) |
| H9 | A/turkey/Wisconsin/1/1966 (H9N2) |
| H10 | A/chicken/Germany/n/1949 (HI 0N7) |
| H11 | A/duck/Memphis/546/1974 (HI 1N9) |
| H12 | A/duck/Alberta/60/1976 (H12N5) |
| H13 | A/gull/Maryland/704/1977 (HI3N6) |
| H14 | A/long-tailed duck/Wisconsin/100S4225/2010 (H14N6) |
| H15 | A/duck/AUS/34 1/1983 (Hi5N8) |
| H16 | A/bl ack-headed gull/Sweden/5/99 (H16N3) |
| H17 | little yellow-shouldered bat/Guatemala/164/2009 (H17N10) |
| H18 | A/flat-faced bat/Per/033/2010 (H18N11) |
| Victoria | B/Brisbane/60/2008 |
| Victoria | B/Miyazake/59/2014 |
| Yamagata | B/T aiwan/18 5/2014 |

TABLE 2

| NA strains used to construct the NA-Bac. | |
| --- | --- |
| NA subtypes | Influenza virus strain |
| N1 | A/Califoria/04/2009 (HIN1) |
| N1 | A/Egypt/2321 -N AMRU3/2007 (H5N1) |
| N2 | A/d uck/Taiwan/a043/2015 (H5N2) |
| N2 | A/chicken/Taiwan/1209/2003 (H5N2) |
| N2 | A/Babol/36/2005 (H3N2) |
| N2 | A/Chicken/Hong Kong/G9/1997 (H9N2) |
| N3 | A/duck/Taiwan/a180/2015 (H5N3) |
| N4 | mallard duck/Alberta/299/1977 (H4N4) |
| N5 | green-winged teal/ALB/199/1991 (H12N5) |
| N6 | A/duck/Taiwan/l 702004/2017 (H5N6) |
| N7 | A/mallard/ALB/196/1996 (H10N7) |
| N8 | A/duck/TW/a068/2015 (H5N8) |
| N9 | A/duck/Anhui/SC702/2013 (H7N9) |
| N10 | A/bat/Guatemala/164/2009 (H17N10) |
| N11 | A/flat-faced bat/Peru/033/201 0 (H18N11) |
| Victoria | B/Brisbane/60/2008 |

Example 3 Characterization of Insect Cells and Baculoviruses Respectively Having Viral Antigen Expressed on their Surfaces

3.1 Confirmation of Antigen Expressions on the Surface of Insect Cells and Baculoviruses After the generation of recombinant baculoviruses as described in Example 2, the expression of each antigen on the infected insect cell surface was confirmed by immunofluorescence assay. An anti-His antibody was used to detect the His6-tag on each recombinant antigen. In contrast to the cells that were non-infected or infected by wild-type baculovirus (wt-Bac), the cells infected with HA-Bac and NA-Bac would display the HA and NA on their surfaces, respectively, on the infected cell surface (FIG. 3, panel (A)). Similarly, cells infected by different GP-Bacs possessing the Ebola-GP expression constructs also exhibited the cell-surface display of Ebola GP proteins (data not shown); while cells infected by D2E-Bac and ZE-Bac showed the cell-surface display of the envelope (E) proteins from Dengue virus type 2 and Zika virus, respectively (data not shown).

Figure 4:
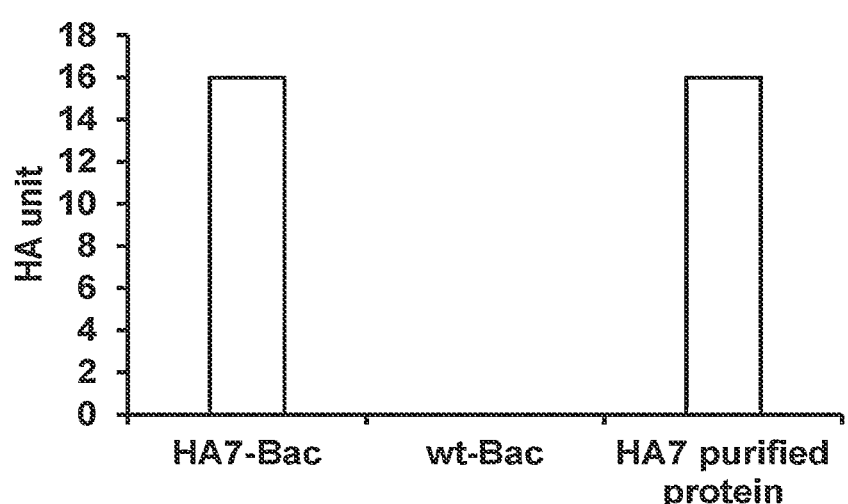
FIG. 4 Hemagglutination activities of HA-Bacs or HA-cells. (A) Hemagglutination assay using the purified baculoviruses. HA7-Bac and wt-Bac were two-fold serial diluted from the titer of $1 \times 10^5$ pfu in a V-bottom 96-well plate and then added with 1% turkey red blood cells. After 30 minutes, HA7-Bac could agglutinate the red blood cells up to the 1:16 dilution (i.e., HA titer=16). wt-Bac showed no detectable hemagglutination activity. One microgram of purified HA7 protein served as a positive control. (B) Hemagglutination assay using the HA-cells. Sf21 cells were infected with each HA-Bac at an MOI=1. The infected cells were collected at 2 d.p.i. and $1 \times 10^6$ infected cells were re-suspended in 1 ml of D-PBS. For hemagglutination assay, 100 µl of cell suspension was added in the initial dilution. One microgram of purified HA7 protein served as a positive control.
Figure 4:
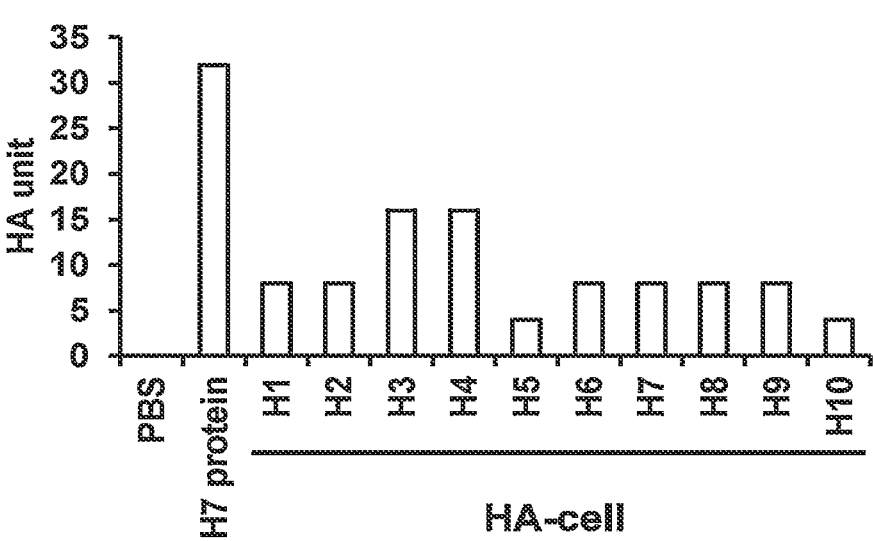

Other than the insect cell membrane, the derived baculo-viruses also had the recombinant proteins displaying on their baculoviral envelopes since the viruses harvested the enve-lope from the infected cells. Each recombinant baculovi-ruses were harvested by sucrose gradient ultracentrifugation and determined the surface-displayed recombinant proteins by immunogold labeling the His6 tag. As there was no colloidal gold labeling on the envelope of wt-Bac, the incorporation of recombinant protein HA, NA, GP, D2E, and ZE was determined on the purified baculovirus particles of HA-Bac, NA-Bac (FIG. 4 panel (B)), as well as in GP-Bacs, D2E-Bac and D2E-Bac (data not shown), respectively.

3.2 Functional Analysis of Insect Cells and Recombinant Baculoviruses

After confirming the surface displays of antigens on insect cells and baculoviruses, whether these recombinant antigens still exhibited their authentic functions were evaluated. For influenza HA, the hemagglutination activity for both recom-binant viruses and infected insect cells was determined. In this assay, the functional HA binds to the sialic acid recep-tors on the surfaces of red blood cells and forms clumps of red blood cell lattices. An HA7-Bac of titer $1\times10^5$ pfu aggregated turkey red blood cells so did the purified HA7 protein, whereas wt-Bac showed no red blood cell aggluti-nation (FIG. 4, panel (A)). Same for the insect cells with HA display, a panel of insect cells displaying different subtypes of HA exhibited at least 4 hemagglutination units (HAU) (FIG. 4, panel (B)). These results confirmed the proper folding and function of recombinant HA on the surface of insect cells and baculoviruses.

Figure 5:
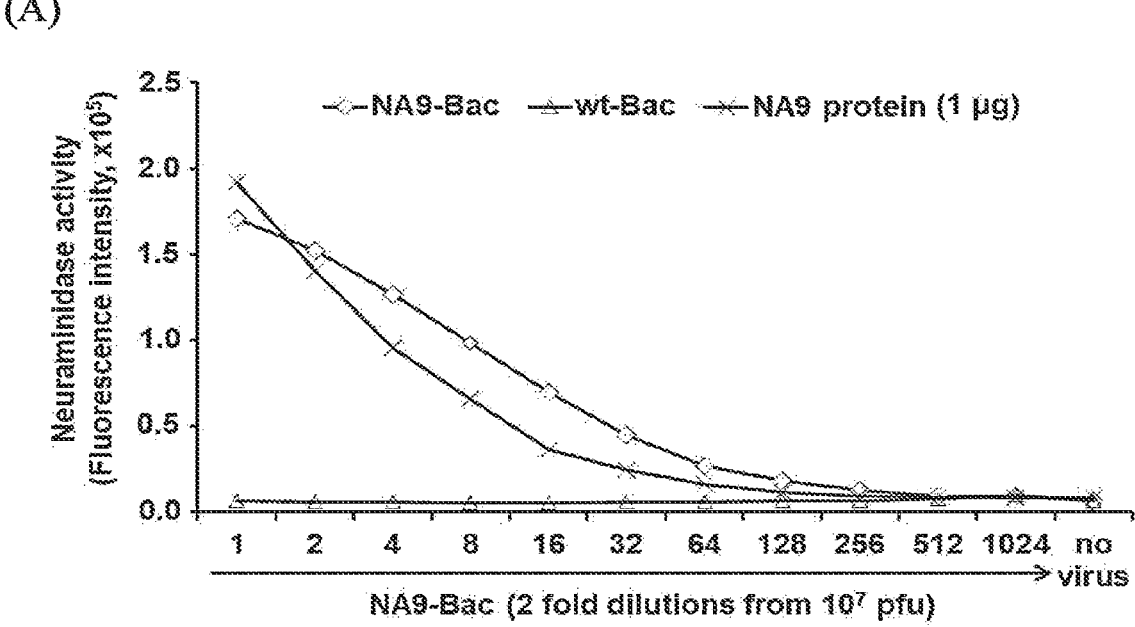
FIG. 5 Neuraminidase activities of NA-Bacs. (A) The neuraminidase activity of NA9-Bac was examined by MUNANA assay. The purified baculoviruses, NA9-Bac and wt-BAC, were two-fold serial diluted from the titer of $1 \times 10^7$ pfu and mixed with MUNANA substrate. After incubation at 37° C. for 1 hour, the fluorescent products derived by NA digestion were determined using an excitation wavelength of 365 nm and an emission wavelength of 450 nm. wt-Bac served as a negative control and 1 µg of purified NA9 protein served as a positive control. (B) Anti-influenza drugs inhibited the neuraminidase activity of NA9-Bac. Two neuraminidase inhibitors, Oseltamivir and Zanamivir, were serially diluted in 10-fold and mixed with $1 \times 10^7$ pfu of NA9-Bac individually. After incubation at 37° C. for 30 minutes, the NA activities were determined by MUNANA assay.
Figure 5:
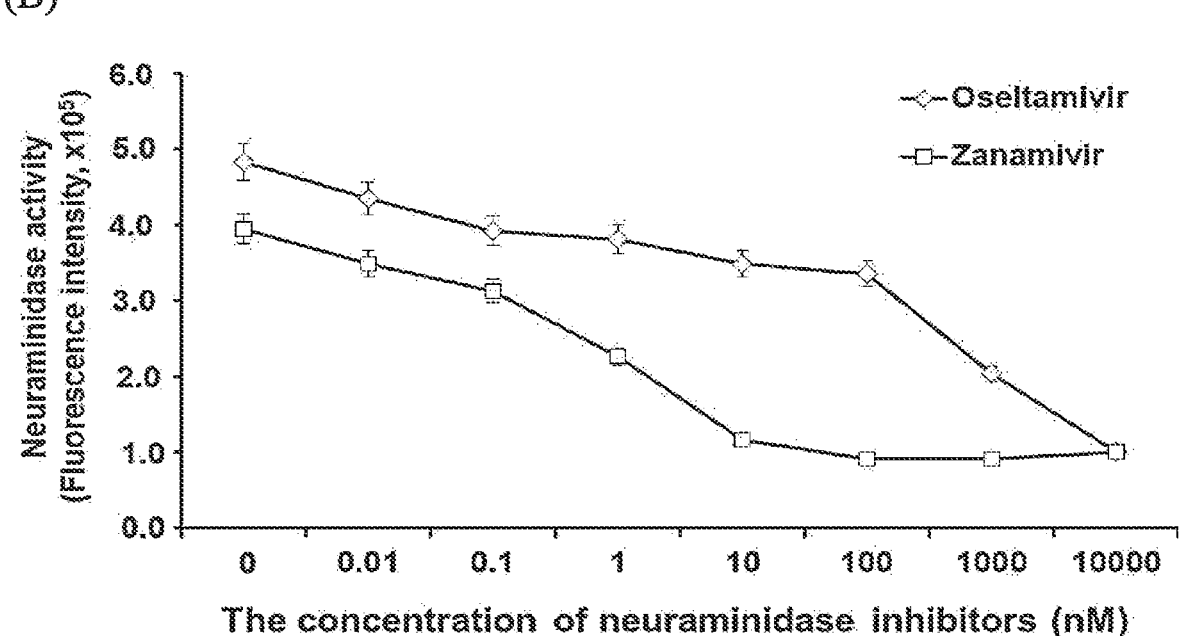
Figure 6:
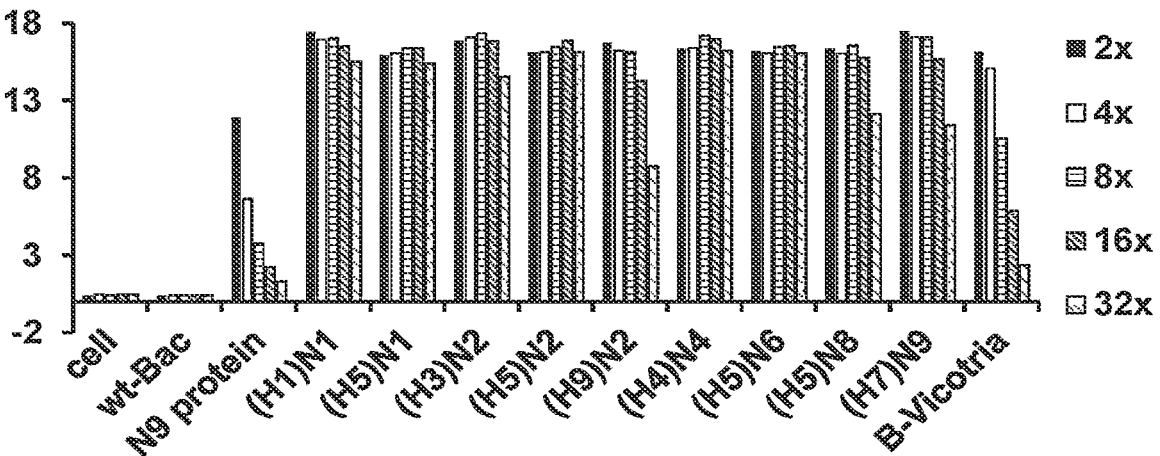
FIG. 6 Neuraminidase activities of NA-cells. NA-cells infected with wt-Bac, and one microgram purified N9 proteins, were 2-fold serial diluted and mixed with MUNANA substrate. After incubation at 37° C. for 1 hour, the fluorescent products derived by NA digestion were determined using an excitation wavelength of 365 nm and an emission wavelength of 450 nm.

To confirm the activity of influenza NA, we determined the NA activity by 2'-(4-Methylumbelliferyl)-α-D-N-acetyl-neuraminic acid (MUNANA) assays. In this assay, func-tional NA cleaves the MUNANA substrate to release the fluorescent product 4-methylumbelliferone (4-MU) which can be detected and quantified by a fluorometer. An NA9-Bac with the initial title of $1\times10^7$ pfu exhibited an NA activity similar to 1 μg of purified NA9 protein as analyzed by MUNANA neuraminidase assays (FIG. 5, (A)). When added with the NA inhibitors Zanamivir (Relenza) and Oseltamivir (Tamiflu), An increase in the concentration of Zanamivir or Oseltamivir was inversely proportional to the neuraminidase activity of NA9-Bac (FIG. 5, (B)). These results indicated the proper function of recombinant NA9 proteins on the baculovirus. We also used NA-cells to perform similar experiments and the NA-cells also exhibited the evident NA activity. All the NA-cells exhibited an NA activity as revealed by serial dilution (FIG. 6).

For the E protein of Dengue viruses and Zika viruses, the induction of syncytium formation, which is a typical cyto-pathic effect of flavivirus infection, was used as a sign of proper E protein function. After the infection of ZE-Bac at an MOI=10, Sf21 cells displayed the formation of multi-nucleated syncytial cells at 3 d.p.i. (data not shown). On the other hand, cells infected with wt-Bac (generated by the empty vector with mCherry reporter gene only) exhibited red fluorescence but did not form syncytia (data not shown). These suggested that the ZE protein on the infected cells induced the syncytium formation.

Figure 7:
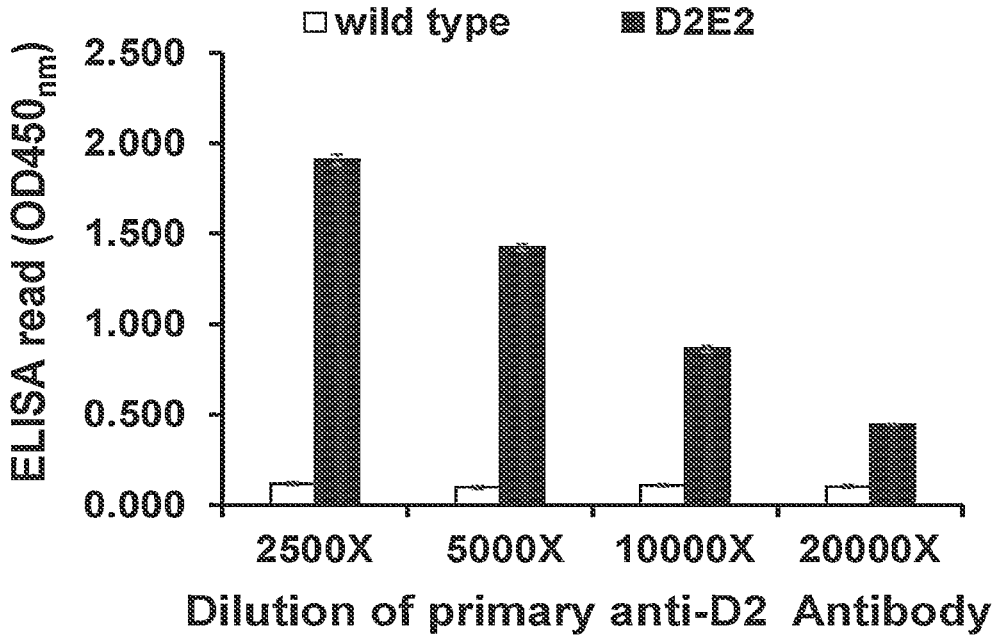
FIG. 7 Cell-based ELISA using D2E-cells characterized the antibody binding. Sf21 cells were infected with D2E-Bac at an MOI=0.5. The cells were fixed on 4 d.p.i by 4% paraformaldehyde. An antibody against Dengue virus type 2 (anti-D2) was diluted at 2,500, 5,000, 10,000, and 20,000 times, respectively, and added to the cells for detecting the antibody binding.
Figure 8:
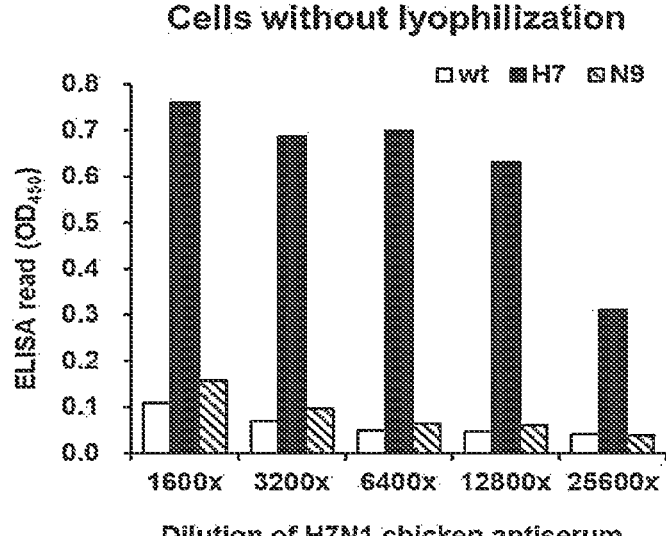
FIG. 8 Cell-based ELISA characterized the type-specific antibodies in an H7N1 chicken antiserum. Sf21 cells were infected with wt-Bac, HA7-Bac, and NA9-Bac at an MOI=1. The cells were fixed on 2 d.p.i by 4% paraformaldehyde and half of the cells were lyophilized in the plate by a freeze drier. An H7N1 chicken antiserum was diluted at 1,600, 3,200, 6,400, 12,800, and 25,600 times, respectively, and added to both cells without lyophilization (panel (A)) and with lyophilization (panel (B)) for detecting the type-specific antibody binding.

Example 4 Use of the Antigen-Displayed Insect Cells or Viruses to Identify Antigen-Specific Antibodies The antigen-displayed insect cells or baculoviruses could serve as convenient tools to identify or characterize the antigen-specific antibodies, either the monoclonal antibodies or the antibodies in sera from infected patients. The infected cells with antigen display can be the antigens of ELISA. Different from conventional ELISA using virus samples or purified proteins as antigens, the cell-based ELISA using infected insect cells did not need the operation of real infectious viruses or the purification of recombinant proteins. Antigens on the cell surface preserved their con-formation and thus it was more possible to identify the antibodies recognizing the conformational epitope. HA5-Bac was used to infect the BmN cells of silkworms. An anti-His antibody could significantly distinguish the insect cells infected with HA5-Bac and those infected with wt-Bac (data not shown). As we applied an antibody that specifically targets the Dengue virus type 2 to the cells infected with D2E-Bac or wt-Bac. The ELISA signals from D2E-cells were significantly higher than those from wt-Bac infected cells and were inversely proportional to antibody dilution factors (FIG. 7). The cell-based ELISA could also be applied to determine the antibodies in sera. We used an H7N1 chicken antiserum to interact with HA7-cells, NA9-cells, and wt-cells. The serum specifically interacted with HA7-cells but not the NA9-cells (FIG. 8). Moreover, the drying of the cells did not affect the ELISA results (FIG. 8, (B)) so these antigen-displayed cells could be preserved and trans-ported easily.

4.1 Influenza Serotyping Using the Present HA- or NA-Cells

Figure 9:
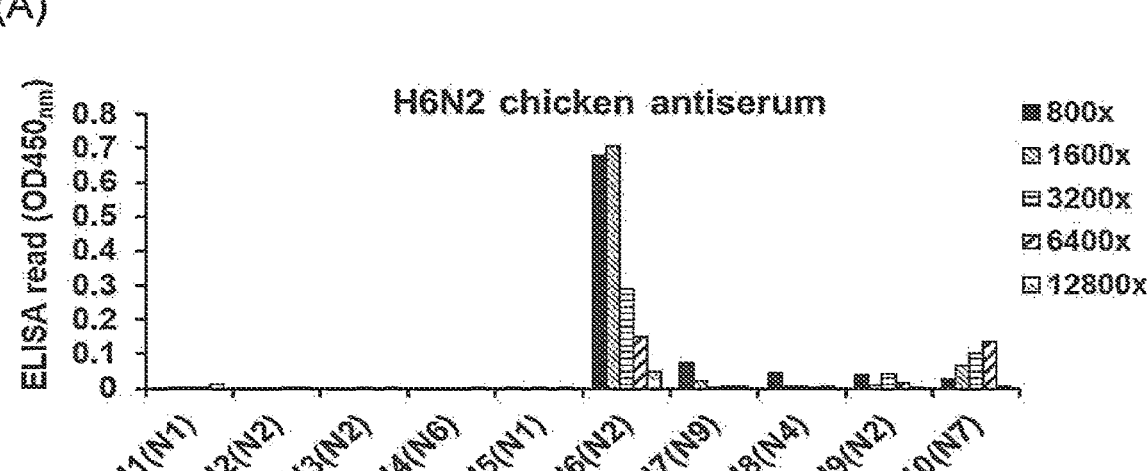
FIG. 9 Cell-based ELISA determined the influenza HA subtype of (A) an H6N2 chicken antiserum and (B) an H7N1 antiserum. Sf21 cells were infected with HA-Bac displaying different subtypes of influenza HA. Each chicken antiserum was diluted from 800 to 12,800 times and added to the cells for detecting the type-specific antibody binding. The final ELISA values were derived by subtracting the absorbance of wt-Bac infected cells from the absorbance of HA-cells.
Figure 9:
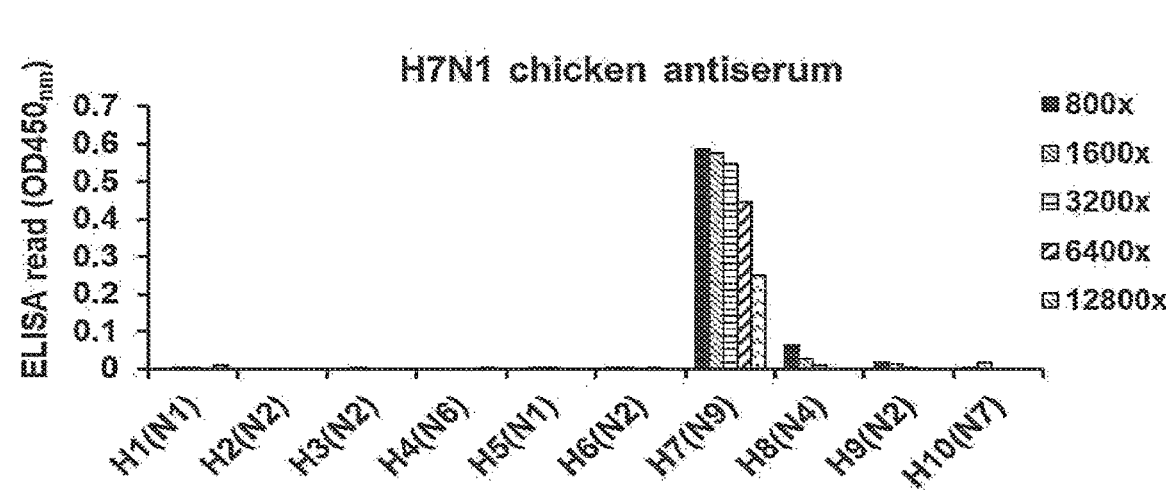
Figure 10:
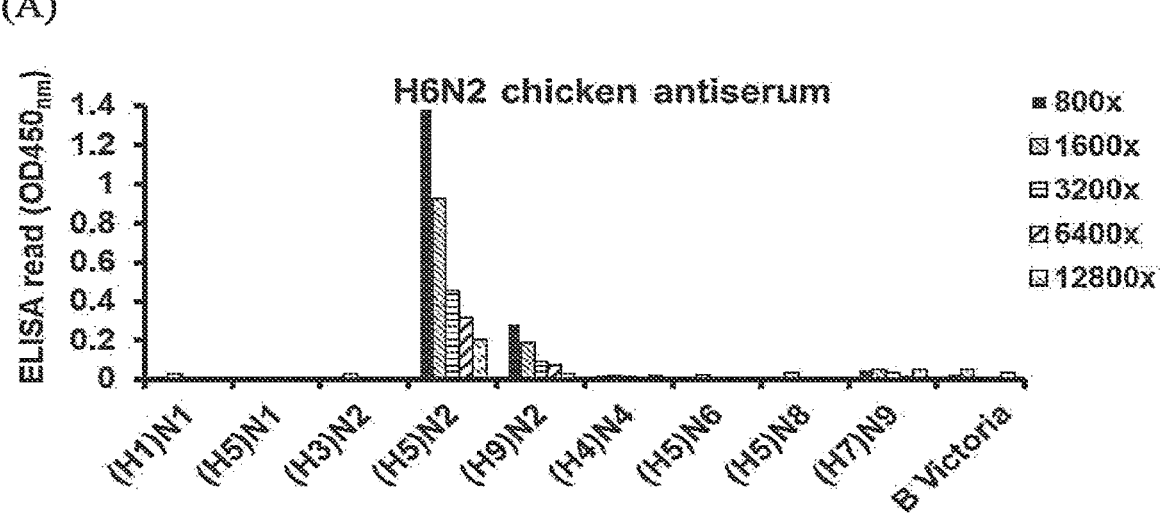
FIG. 10 Cell-based ELISA determined the influenza NA subtype of (A) an H6N2 chicken antiserum and (B) an H7N1 antiserum. Sf21 cells were infected with NA-Bac displaying different subtypes of influenza NA. Each chicken antiserum was diluted from 800 to 12,800 times and added to the cells for detecting the type-specific antibody binding. The final ELISA values were derived by subtracting the absorbance of wt-Bac infected cells from the absorbance of NA-cells.
Figure 10:
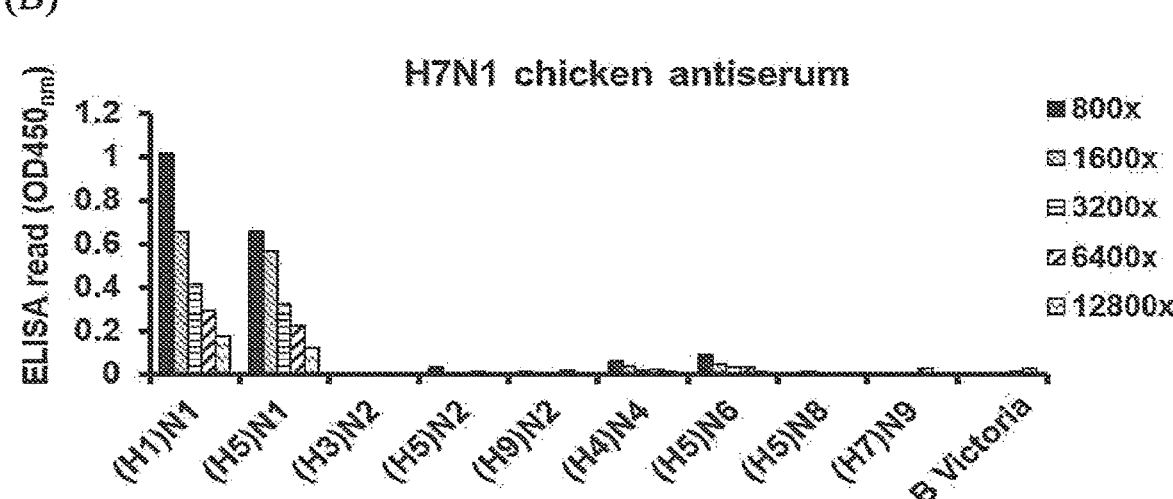

With HA- and NA-cells displaying different subtypes of HA and NA, respectively, they are useful for detecting the subtype of influenza infection of an antibody or sera of patients. When an H6N2 and an H7N1 chicken antiserum interacted with HA-cells, these two sera specifically inter-acted with H6-cells (FIG. 9, (A)) and H7-cells (FIG. 9, (B)), respectively. When applied to interact with NA-cells, H6N2 antiserum interacted with (H5)N2-cells and (H9)N2-cells (FIG. 10, (A)), and H7N1 antiserum interacted with (H1) N1-cells and (H5)N1-cells (FIG. 10, (B)). H6N2 antiserum did not interact with (H3)N2-cells, probably because the N2 of H3N2 belongs to a human-infectious influenza virus and its N2 sequence is far different from that of avian influenza viruses H5N2 and H9N2. These results confirmed that cell-based ELISA could be applied to determine the specific influenza subtypes of an antiserum.

4.2 Serum Antibody Detection

In this example, HA cells displaying HA from 3 influenza A viruses and 3 influenza B viruses, and the spike (S) and nucleocapsid (N) proteins from SARS-CoV-2 virus were used to detect serum samples from influenza patients or vaccinees.

Figure 11:
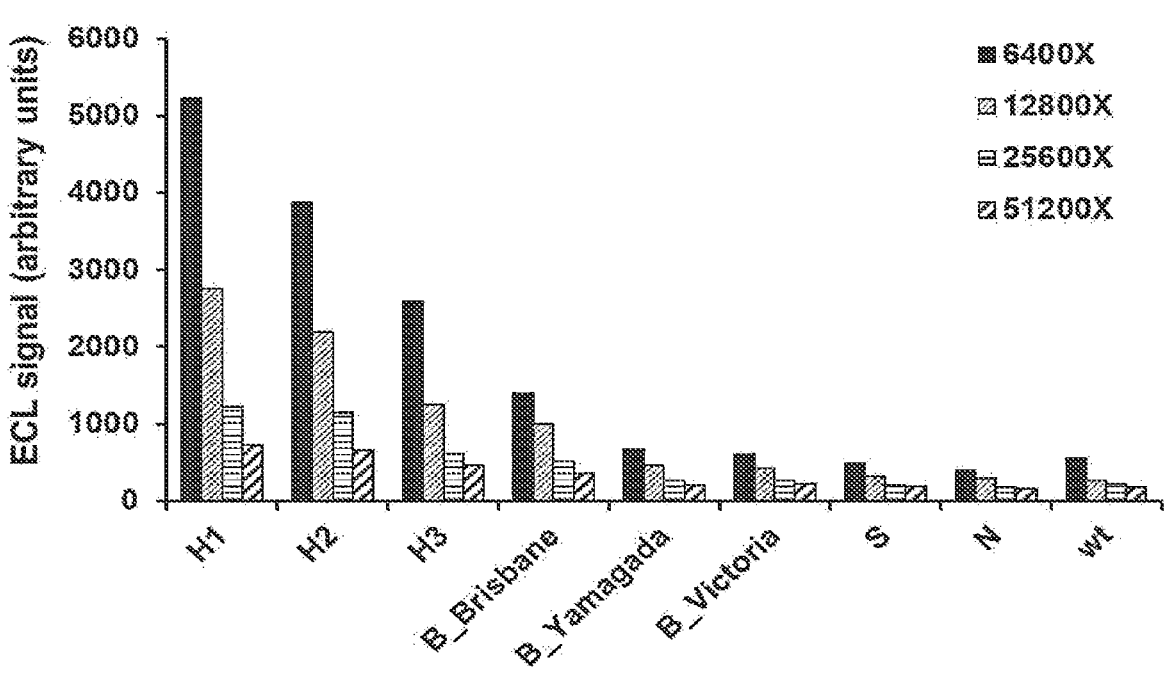
FIG. 11 ECLIA determined the antibody responses of an influenza vaccinee. Sf21 cells infected with HA-Bac of 3 influenza A viruses and 3 influenza B viruses, and baculoviruses displaying the spike (S) and nucleocapsid (N) proteins from SARS-CoV-2 virus, and wt-Bac were employed as antigens in MSD ECLIA. The serum sample was diluted from 6,400 to 51,200 times and added to the cells for detecting the type-specific antibody binding. The results of ECLIA were expressed in arbitrary units.
Figure 12:
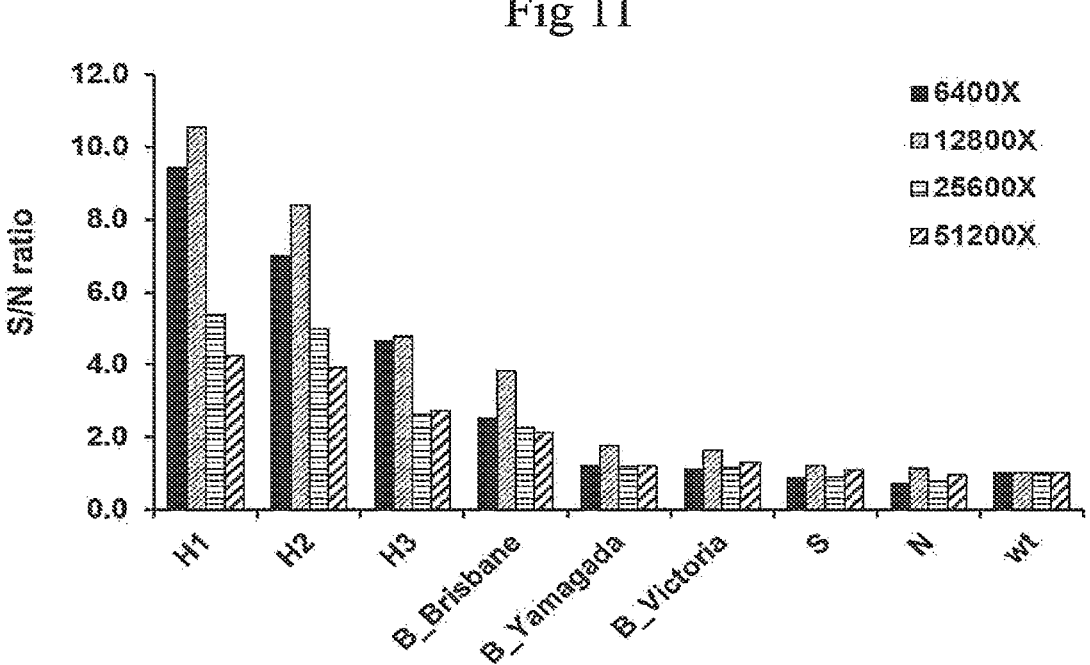
FIG. 12 Signal-to-noise (S/N) ratio of ECLIA results. Signals derived from ECLIA in FIG. 11 were used to calculate the S/N ratio by dividing the signal of wt-cells. S/N>2 is considered to be positive.

To this purpose, HA cells were seeded in multi-array microplates in Meso Scale Discovery (MSD) electrochemi-luminescent detection system, serum samples were then added to react with the antigen-displaying cells, after tradi-tional ELISA procedures, the secondary antibody conju-gated with SULFO-TAG labels were then added. During detection, electricity applied to the plate electrodes leads to light emission by SULFO-TAG labels, allowing for ultra-sensitive detection. Serum from an influenza vaccinee was used as an example. Significant antibody responses were observed in H1-, H2-, and H3-cells, and a slightly lower signal from a type B HA-cells (FIG. 11). Notably, with an initial seeding of $4\times10^4$ cells in the well of microplates, the serum sample could be diluted up to 51,200 folds, however, a signal-to-noise (S/N) ratio (calculated by dividing the signal of wt-cells) over 2 was still observed when interacting with these cells (FIG. 12).

Figure 13:
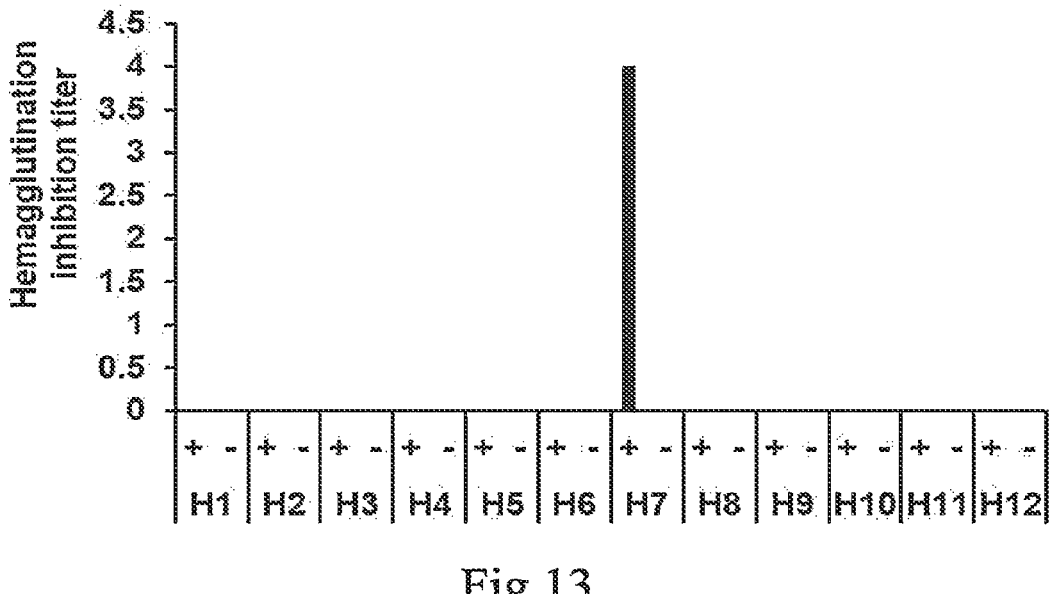
FIG. 13 Hemagglutination inhibition (HI) assay using HA-cells. HA-cells expressing different subtypes of HA were used to determine the inhibition effect of an H7N9 monoclonal antibody on the hemagglutination activity. The antibody was two-fold serially diluted from an initial content of 1 g (i.e., wells in the first row contained 0.5 g of antibody). HA-cells with 8 hemagglutination units (HAU) were added to each well with or without the antibody. After 30 minutes of incubation at room temperature, the HI titer was recorded as the reciprocal of the highest antibody dilution that inhibited the hemagglutination reaction.
Figure 14:
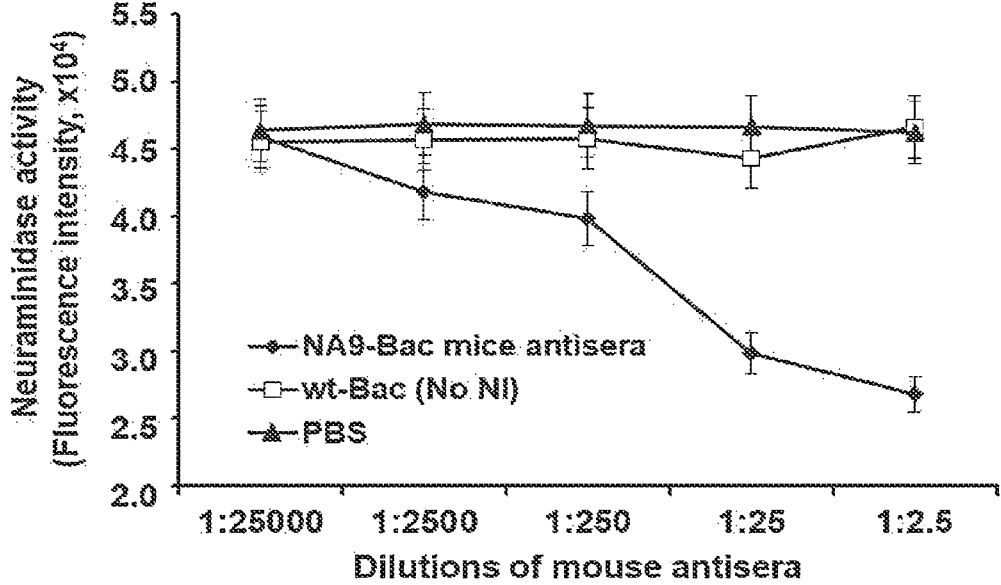
FIG. 14 NA-Bac was used for neuraminidase inhibition (NI) analysis to identify NA subtypes or NA antibody specificity. Mouse antisera collected from mice immunized intraperitoneally with $1 \times 10^9$ pfu of NA9-Bac or wt-Bac, or phosphate-buffer saline (PBS) were diluted and mixed with $1 \times 10^7$ pfu of NA9-Bac, respectively. After incubation at 37° C. for 30 minutes, NA9 activities were determined by MUNANA analysis.

In addition, an anti-H7 monoclonal antibody specifically inhibited the hemagglutination of H7-cells but not the other HA-cells, and the serial dilution of the antibody revealed the hemagglutination inhibition (HI) titer as 4 (FIG. 13). Mouse antisera collected from mice immunized with NA9-Bac inhibited the MUNANA cleavage enzymatic activity of NA9-Bac, whereas the antisera from mice immunized with wt-Bac or PBS did not (FIG. 14). Similarly, the infected sera of patients can be characterized by these HI or neuraminidase inhibition (NI) assays.

Example 5 Use of Baculoviruses Displaying Viral Antigen to Produce Highly Functional mAbs Neutralizing mAbs that inhibit the infection of viruses have shown to be clinically effective in the treatment of Varicella-zoster virus (VZV), Hepatitis B virus (HBV), Rabies virus (RABV) and Respiratory syncytial virus (RSV). We examined the potential of using our HA7-Bac and NA9-Bac to be the antigens for producing mAbs. Two groups of female BALB/c mice (n=3) were immunized intraperitoneally with $1\times10^9$ pfu purified HA7-Bac and NA9-Bac, respectively. For negative controls, the other two groups of mice were injected with purified wt-Bac ($1\times10^9$ pfu) and phosphate buffer saline (PBS), respectively. Followed by two boosters with two-week intervals, the splenocytes of immunized mice were collected and fused with mouse myeloma cells. Single hybridoma clones secreting specific mAb were isolated by 2-3 rounds of limiting dilution. To characterize the binding specificities of each mAb, we transiently expressed viral HA7 and NA9 proteins in A549 cells by plasmid transfection and used these A549 cells to perform the cell-based ELISA for the isolated mAbs.

Figure 15:
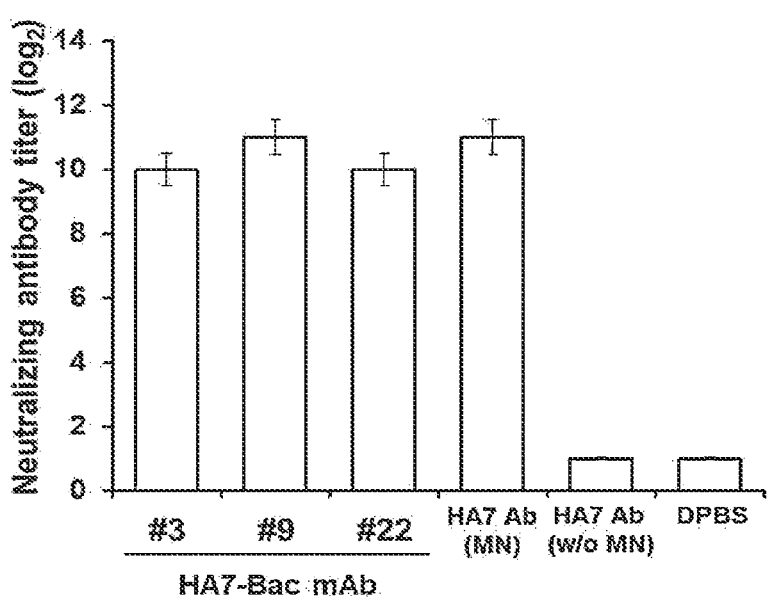
FIG. 15 Monoclonal antibodies (mAbs) derived from HA-Bac and NA-Bac exhibited neutralization or inhibition function toward influenza infections. (A) Microneutralization assay of three HA7-Bac derived mAbs (HA7-Bac mAb #3, 9, and 22) against the H7N9 influenza virus (A/Taiwan/01/2013) infection. The mAbs were two-fold serial diluted and mixed with 10×50% tissue culture infective doses (TCID$_{50}$) of H7N9 influenza viruses to determine microneutralization titers (the reciprocal of the highest dilution without CPE) in the infected MDCK cells. A commercial mAb with microneutralization (MN) activity was used as the positive control and a commercial mAb without microneutralization (w/o MN) was used as the negative control. (B) Enzyme-Linked Lectin assay (ELLA) of three NA9-Bac derived mAbs (NA9-Bac mAb #8, 38, and 40) measuring the inhibition of NA9 activity. The mAbs were two-fold serial diluted and mixed with $10^7$ pfu of NA9-Bac. The mixtures were then added into 96 well plates coated with fetuin. After incubation of 16-18 hours, horse radish peroxidase-labeled peanut agglutinin was added to bind the exposed galactose. TMB substrate was added 2 hours after to determine the enzymatic cleavage of fetuin by NA proteins of NA9-Bac. The percent inhibition of NA enzymatic activity was calculated by comparing the values to NA9-Bac mixed with Control IgG.
Figure 15:
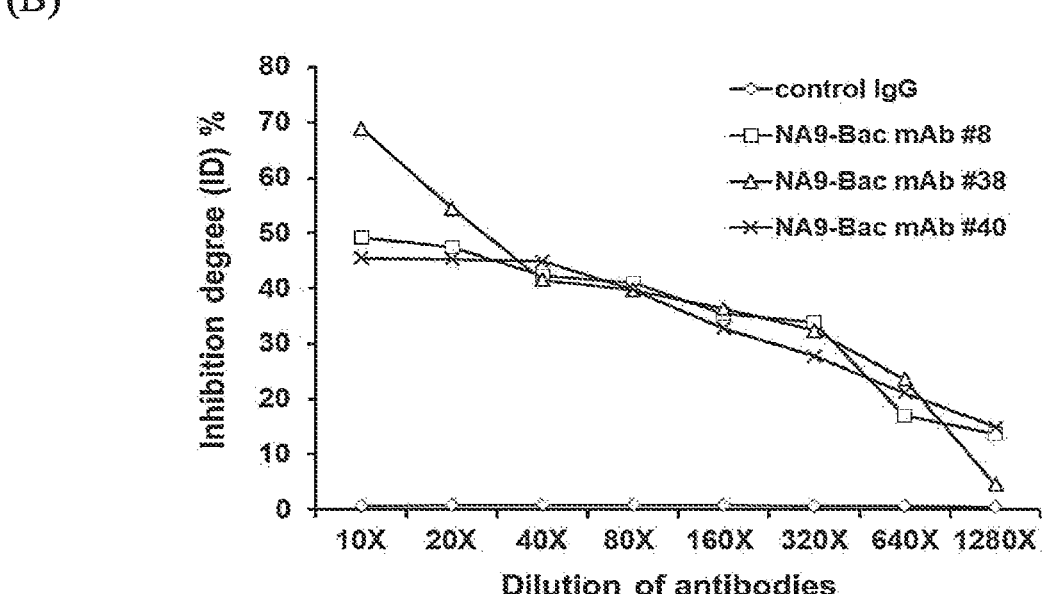

We initially isolated 82 and 105 mAb clones from hybridoma derived from the injection of HA7-Bac and NA9-Bac (data not shown), respectively. In the cell-based ELISA, 39 HA7-Bac derived and 60 NA9-Bac derived mAbs exhibited higher binding specificities to HA7-Bac and NA9-Bac (data not shown). Since antibodies targeting the HA may neutralize the virus infection, we selected three HA7-Bac mAbs to examine their neutralizing activity against live H7N9 influenza virus infection to MDCK cells. HA7-Bac mAb #3, 9, and 22 exhibited the comparable neutralization ability similar to a commercial mAb with microneutralization (MN) activity whereas the other commercial mAb without MN activity showed no neutralization effect (FIG. 15, (A)). Antibodies targeting NA also have the potential to reduce virus infection by blocking the NA sialidase activity, which is essential for virus budding. In an enzyme-linked lectin assay (ELLA) detecting NA enzymatic activity, NA9-Bac mAb #38 showed effective inhibition of NA9 activity followed by mAb #8 and 40 whereas the control IgG had no sign of inhibition (FIG. 15, panel (B)). The median (50%) inhibition concentrations of NA9-Bac mAb #8, 38, and 40 were calculated as 1, <0.5, and 0.5 mg/ml, respectively

Example 6 Baculoviruses Displaying Viral Antigen Provide the Timely Vaccine Antigens The viral surface proteins are usually primary viral components inducing protective immune responses upon being vaccine antigens, for example, the influenza HA and NA. To explore the prophylactic protection effect of HA7-Bac and NA9-Bac against influenza H7N9 infection, we immunized mice with HA7-Bac, NA9-Bac or wt-Bac ($10^9$ pfu per shot). Mice immunized with PBS only served as the negative control. After two boosters with two-week intervals, all the immunized groups were challenged with mouse-adapted H7N9 virus (A/Taiwan/01/2013) ($10\times50\%$ mouse lethal dose ($MLD_{50}$) per mouse) 8 weeks after the primary immunization. Results are summarized in Table 3.

The immunization of wt-Bac did not protect mice from death as all the mice died at day 6 post-challenge, nor did the PBS-immunized group. NA9-Bac immunized group showed a 6000 survival rate from day 7 post-challenge. In contrast, HA7-Bac immunized mice all survived the H7N9 challenge as the mice immunized with 10 µg purified HA7 proteins.

TABLE 3

Mice immunized with HA7-Bac or NA9-Bac survived the lethal
H7N9 influenza infection

| Day(s) post immunization | Survival (%) | | | | |
| | HA7-Bac | HA7 purified protein (10 µg/shot) | NA9-Bac | Wi-Bac | PBS only |
| --- | --- | --- | --- | --- | --- |
| D0 | 100 | 100 | 100 | 100 | 100 |
| D1 | 100 | 100 | 100 | 100 | 100 |
| D2 | 100 | 100 | 100 | 100 | 100 |
| D3 | 100 | 100 | 100 | 100 | 100 |
| D4 | 100 | 100 | 100 | 100 | 100 |
| D5 | 100 | 100 | 100 | 40 | 40 |
| D6 | 100 | 100 | 100 | 0 | 0 |
| D7 | 100 | 100 | 60 | 0 | 0 |
| D8 | 100 | 100 | 60 | 0 | 0 |
| D9 | 100 | 100 | 60 | 0 | 0 |
| D10 | 100 | 100 | 60 | 0 | 0 |
| D11 | 100 | 100 | 60 | 0 | 0 |
| D12 | 100 | 100 | 60 | 0 | 0 |
| D13 | 100 | 100 | 60 | 0 | 0 |
| D14 | 100 | 100 | 60 | 0 | 0 |

Example 7 Detecting Anti-SARS-CoV-2 Antibodies in Serum Samples 7.1 Construction of Recombinant Baculoviruses for Surface Display of SARS-CoV-2

In this example, two recombinant baculoviruses independently displayed the N and S proteins of SARS-CoV-2 on its surface, i.e., N-Bac and S-Bac, were generated in accordance with the construct of FIG. 16. Note that the transmembrane (TM) and cytoplasmic tailed domain (CTD) of GP64, the surface glycoprotein of baculovirus, were fused to the C-termini of full-length N and the S ectodomain. These recombinant antigens could then be secreted and anchored on the plasma membrane of insect cells or the baculovirus envelope by the TM of GP64. Indeed, we detected recombinant N and S in purified N-Bac and S-Bac baculoviruses (data not shown), as well as on the surface of insect cells infected by N-Bac and S-Bac (designated as N-Cells or S-Cells, respectively), but not the cells infected by wild-type AcMNPV (wt-Cells) (data not shown).

7.2 Surface Display of Antigens on Insect Cells for Serum Analyses

To test if N-Cells and S-Cells could be used as antigens for serum antibody determination, we collected sera from 11 real-time reverse transcription-polymerase chain reaction (RT-PCR)-confirmed COVID-19 patients in Taiwan during their hospitalizations. The samples were collected 13-59 days after symptoms onset (Table 4).

TABLE 4

COVID-19 patient data

| Patient no. | Age | Gender | Days post symptom onset upon sample being drawn | Symptoms |
|---|---|---|---|---|
| 1 | 23 | M | 17 | Fever, cough, rhinorrhea |
| 2 | 41 | F | 30 | Fever, cough, rhinorrhea, headache, sore throat, diarrhea, chest pain |
| 3 | 23 | F | 13 | Distorted sense of smell, rhinorrhea |
| 4 | 54 | M | 21 | Cough. sore throat, diarrhea |
| 5 | 33 | M | 38 | Fever, cough, headache, sore throat, diarrhea, chest pain, dyspnea, chills, nausea |
| 6 | 21 | F | 22 | Fever, cough, distorted sense of taste and smell, headache, myalgia, rhinorrhea, sore throat, diarrhea, chest pain, dyspnea, chills, nausea |
| 7 | 21 | F | 34 | Fever, cough, distorted sense of taste and smell, diarrhea, chest pain, dyspnea |
| 8 | 64 | M | 32 | Fever, cough, rhinorrhea, diarrhea |
| 9 | 34 | M | 43 | Cough, distorted sense of taste, distorted sense of smell |
| 10 | 50 | F | 29 | Fever, chills, distorted sense of taste |
| 11 | 28 | F | 59 | Cough, rhinorrhea, distorted sense of smell, diarrhea |

N-Cells and S-Cells were first employed in a Western blotting analysis to determine anti-N and anti-S antibody levels in the serum. Compared to 10 healthy control patients that showed no sign of these antibodies, we detected anti-N antibodies in all sera taken from infected patients (although some presented relatively weak signals) (data not shown). In contrast, anti-S antibodies were only clearly detected in the sera of four infected patients (PT-2, 7, 8, and 10), being either weak or absent in the remaining seven samples (data not shown).

Figure 17:
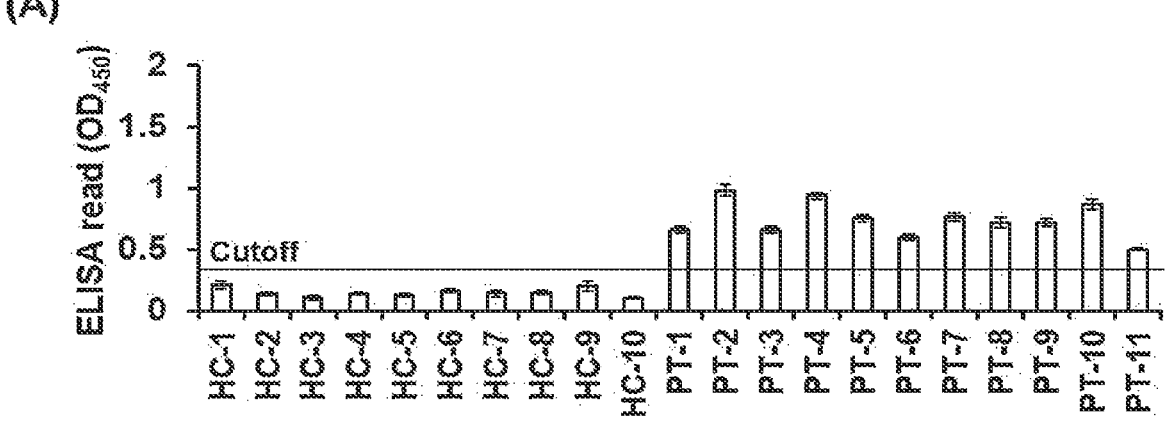
FIG. 17 Detection of SARS-CoV-2-infected patient sera using N-Cells and S-Cells. Detection of SARS-CoV-2 infection using cell-based ELISA. Serum samples (1:200 dilution) of 10 healthy controls (HC) and 11 patients (PT) were subjected to cell-based ELISA using N-Cells (A) or S-Cells (B). Reads have been normalized to the read derived from individual serum interacting with wt-Cells. Dotted line: cutoff value using the mean+3SD of HC samples.
Figure 17:
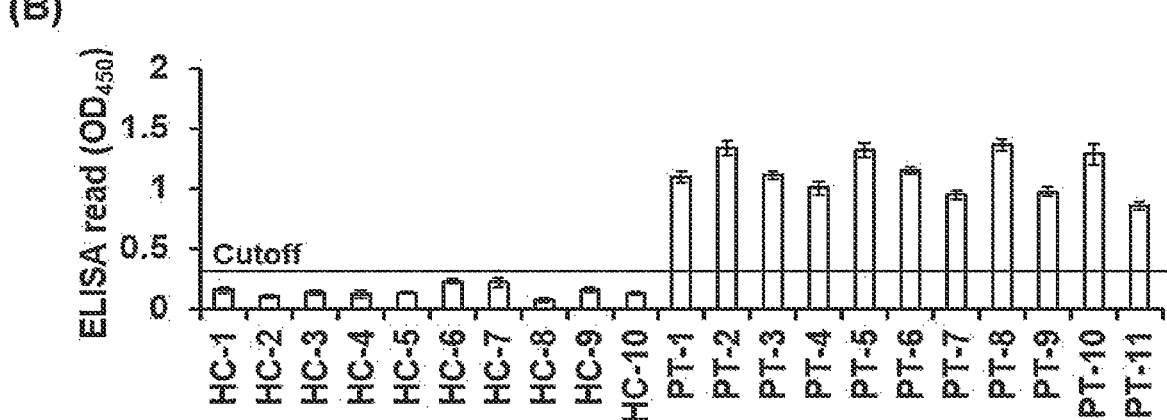

As the denaturing Western blot analysis might overlook conformation-dependent antibodies, we developed a novel cell-based enzyme-linked immunosorbent assay (ELISA) by directly seeding the N-Cells, S-Cells, and wt-Cells into 96-well plates to determine the possible existence of conformational antibodies in the patient sera. Each serum sample interacted with these cells in parallel. The absorbance of wt-Cells was subtracted from those of N-Cells and S-Cells to represent final ELISA values. The mean ELISA value established from all healthy controls plus three standard deviations (SD) was set as the cutoff for each ELISA system (FIG. 17). The sera of all 11 patients were tested positive in ELISA using both N-Cells (FIG. 17, (A)) and S-Cells (FIG. 17, (B)). The N and S proteins on insect cells explicitly interacted with the serum generated by SARS-CoV-2 infection, as antibodies from other human coronaviruses or viruses causing upper respiratory tract infections, as well as serum from an influenza patient, did not generate significant ELISA signal. Strikingly, anti-S antibodies were detectable in all 11 COVID-19-infected patients and at levels different from our Western blotting analysis (data not shown).

These results indicate that SARS-CoV-2 infection generates abundant anti-S antibodies that recognize conformational epitopes, and our cell-based ELISA can readily detect these antibodies.

Figure 18:
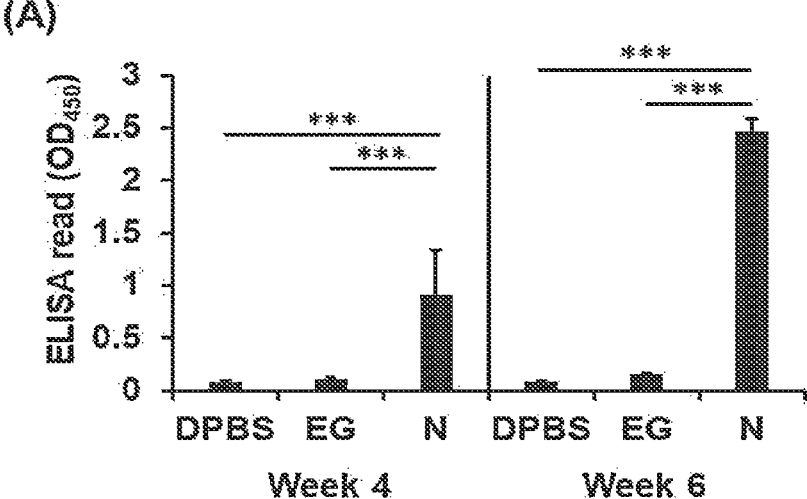
FIG. 18 N-Bac and S-Bac as potential COVID-19 vaccines. Indirect ELISA against purified N (A) or S1 (B) to determine the levels of specific anti-N and anti-S1 IgG antibodies in mice immunized with DPBS (n=5), EG-Bac (n=5), N-Bac (n=10), or S-Bac (n=10). Two-tailed t-test: *P<0.05; P<0.01; *P<0.001.
Figure 18:
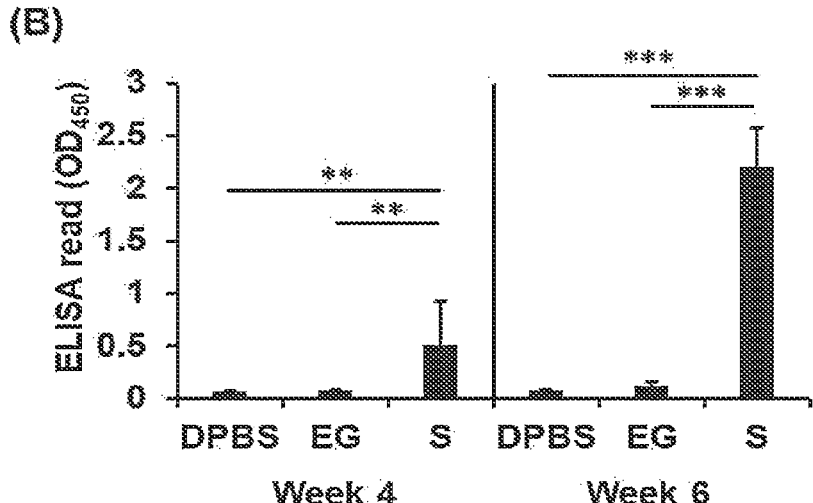
Figure 19:
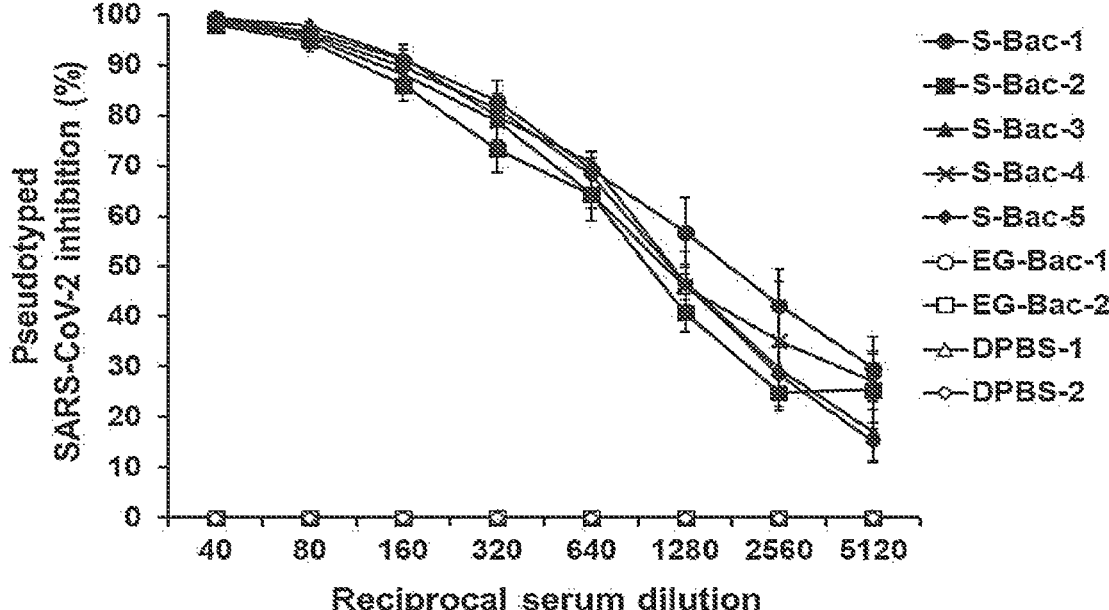
FIG. 19 Neutralizing activities of mouse sera against SARS-CoV-2 pseudovirus. Percent inhibition of pseudovirus infection into HEK293T cells was determined relative to the virus without serum addition. Mean values±SD from three independent experiments is shown.

7.3 Baculovirus Having Viral Antigens Displayed on their Surfaces as Potential Vector Vaccines To evaluate the potential of using N-Bac and S-Bac as vaccine antigens, we immunized mice with the recombinant baculoviruses and then examined the antibodies generated in mouse sera that are specific to S and N proteins. In contrast to mice immunized with Dulbecco's phosphate-buffered saline (DPBS) or baculovirus expressing green fluorescent protein (EG-Bac), mice immunized with N-Bac or S-Bac developed high levels of antibodies recognizing the N and S1 antigens, respectively (FIG. 18). We adopted a neutralization test with lentivirus-based SARS-CoV-2 pseudovirus to test the infection inhibitory effect of mouse antisera. As determined by serial dilution, the sera of mice immunized with S-Bac inhibited pseudovirus infection in HEK293T cells, with 50% inhibition achieved at a dilution of 640-1, 280 folds (FIG. 19). Antisera from N-Bac immunization did not inhibit infectivity since the pseudovirus only harbors S protein from SARS-CoV-2.

These results demonstrate that N-Bac and S-Bac are antigenic and that the antibodies induced by S-Bac can well-neutralize the function of SARS-CoV-2 S protein.

In conclusion, a baculovirus-based virus library was established to display the antigens from all infectious viruses possibly to be collected. One to several antigens from individual viral families were displayed on the surface of recombinant baculoviruses and their infected insect cells from all the 29 viral families. The displayed antigens exhibited authentic protein functions and therefore are useful tools to characterize mAbs or identify infections. Further, these recombinant viruses also served as the antigens for the production of high-quality neutralizing mAbs, which protected the immunized animals against the virus infection. In summary, this recombinant baculovirus virus library can replace the original dangerous virus to assist the prevention and control of virus infections.

It will be understood that the above description of embodiments is given by way of example only and that various modifications may be made by those with ordinary skill in the art. The above specification, examples, and data provide a complete description of the structure and use of exemplary embodiments of the invention. Although various embodiments of the invention have been described above with a certain degree of particularity, or with reference to one or more individual embodiments, those with ordinary skill in the art could make numerous alterations to the disclosed embodiments without departing from the spirit or scope of this invention.

What is claimed is:

1. A recombinant baculovirus comprising:

a promotor consisting of the promoter of the p10 gene and the promoter of the hr1-hsp70 gene;

a first nucleic acid operably linked to the promoter, wherein the first nucleic acid encodes the S or N protein of a coronavirus to be expressed on the outer surface of the recombinant virus;

a second nucleic acid disposed upstream to the first nucleic acid encoding a signal peptide selected from the group consisting of a honeybee melittin signal peptide (HM/HBM), a GP64 signal peptide, a cecropin B signal peptide, and a GRP78/Bip signal peptide, and a third nucleic acid encoding a transmembrane domain and a cytoplasmic tail domain of a baculovirus glyco-protein GP64 operably linked to the promotor.

2. An insect cell infected by the recombinant baculovirus of claim 1, thereby expressing the exogenous viral protein on its outer surface.

3. A method of detecting an antibody in a biological sample comprising:

capturing the antibody with the recombinant baculovirus of claim 1 by an enzyme-linked immunosorbent assay (ELISA), fluorescence-based assay, or flow cytometry screening.

4. The method of claim 3, wherein the biological sample is selected from the group consisting of a whole blood sample, a plasma sample, a serum sample, a urine sample, a mucus sample, and purified or filtered forms thereof.

5. The method of claim 3, wherein the antibody is an IgA, IgM or IgG.

6. A method of detecting an antibody in a biological sample comprising:

capturing the antibody with the insect cell of claim 2 by ELISA, fluorescence-base assay, flow cytometry screening, syncytium formation, or inhibition of the syncytium formation.

7. The method of claim 6, wherein the biological sample is selected from the group consisting of a whole blood sample, a plasma sample, a serum sample, a urine sample, a mucus sample, and purified or filtered forms thereof.

8. The method of claim 6, wherein the insect cell is freeze-dried, vacuum-dried, or spray-dried into lyophilized powders.

9. The method of claim 6, wherein the insect cell is treated with a detergent to expose the exogenous viral protein.

10. The method of claim 6, wherein the antibody is an IgA, IgM or IgG.

* * * * *